US008373140B2

(12) United States Patent
Tokhtuev et al.

(10) Patent No.: US 8,373,140 B2
(45) Date of Patent: Feb. 12, 2013

(54) FLUOROMETRIC SENSOR

(75) Inventors: Eugene Tokhtuev, Duluth, MN (US);
William M. Christensen, Hibbing, MN (US); Christopher J. Owen, Duluth, MN (US); Viktor Slobodyan, Duluth, MN (US); Anatoly Skirda, Hermantown, MN (US)

(73) Assignee: Ecolab USA Inc., St. Paul, MN (US)

( * ) Notice: Subject to any disclaimer, the term of this patent is extended or adjusted under 35 U.S.C. 154(b) by 372 days.

(21) Appl. No.: 12/750,806

(22) Filed: Mar. 31, 2010

(65) Prior Publication Data
US 2011/0240886 A1  Oct. 6, 2011

(51) Int. Cl.
*G01N 21/64* (2006.01)

(52) U.S. Cl. .................................... 250/461.1

(58) Field of Classification Search ............... 250/461.1
See application file for complete search history.

(56) References Cited

U.S. PATENT DOCUMENTS

| 4,783,314 | A  | 11/1988 | Hoots et al. |
| 4,988,375 | A  | 1/1991  | Bornhauser |
| 6,255,118 | B1 | 7/2001  | Alfano et al. |
| 6,369,894 | B1 | 4/2002  | Rasimas et al. |
| 6,831,745 | B2 | 12/2004 | Marquardt et al. |
| 6,842,243 | B2 | 1/2005  | Tokhtuev et al. |
| 6,977,729 | B2 | 12/2005 | Marquardt et al. |
| 7,095,500 | B2 | 8/2006  | Banks |
| 7,154,603 | B2 | 12/2006 | Banks |
| 7,179,384 | B2 | 2/2007  | Moriarty et al. |
| 7,198,755 | B2 | 4/2007  | Tokhtuev et al. |
| 7,220,382 | B2 | 5/2007  | Godfrey et al. |
| 7,550,746 | B2 | 6/2009  | Tokhtuev et al. |
| 2003/0117623 | A1 | 6/2003 | Tokhtuev et al. |
| 2005/0229698 | A1 | 10/2005 | Beecroft et al. |
| 2006/0198761 | A1* | 9/2006 | Tokhtuev et al. ......... 422/82.05 |
| 2006/0246595 | A1 | 11/2006 | Banks et al. |
| 2008/0030712 | A1* | 2/2008 | Tokhtuev et al. ............ 356/51 |
| 2009/0212236 | A1 | 8/2009 | Tokhtuev et al. |
| 2009/0283698 | A1 | 11/2009 | Chapman |

FOREIGN PATENT DOCUMENTS
WO  2007143047 A1  12/2007

OTHER PUBLICATIONS

International Search and the Written Opinion, dated Sep. 29, 2011 for PCT Application No. PCT/IB2011/051344 7 pages).
Turner Designs, Aquafluor Handheld Fluorometer and Turbidimeter User's Manual, Sep. 2004, Version 1.3, pp. 1-36.
Nalco, Traced Antiscalant Control with RO-TRASAR, http://www.extranet.nalco.com/ASP/applications/membrane_tech/equipment/ro_trasar.asp, pp. 1-2.
Turner BioSystems, Picofluor Handheld Flurorometer Operating Manual, Feb. 2010, Version 1.5, pp. 1-16.

* cited by examiner

*Primary Examiner* — David Porta
*Assistant Examiner* — Hugh H Maupin
(74) *Attorney, Agent, or Firm* — Fredrikson & Byron, PA

(57) ABSTRACT

Embodiments provide an optical sensor head and method of making an optical sensor head. In some cases the sensor head can be used as a fluorometric sensor to measure concentrations of substances within a liquid sample of interest. The sensor head includes a light source window and a detector window that transmit light between the sensor head and an analytical area. In some cases the windows include a ball lens positioned within a channel such that the ball lens and the channel create a seal between the interior and exterior of the sensor head.

34 Claims, 18 Drawing Sheets

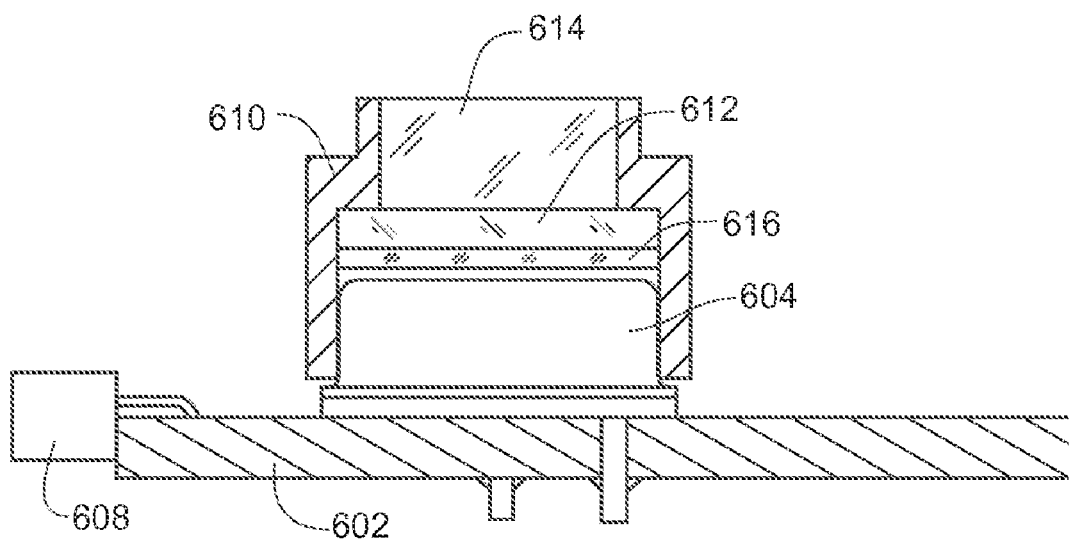

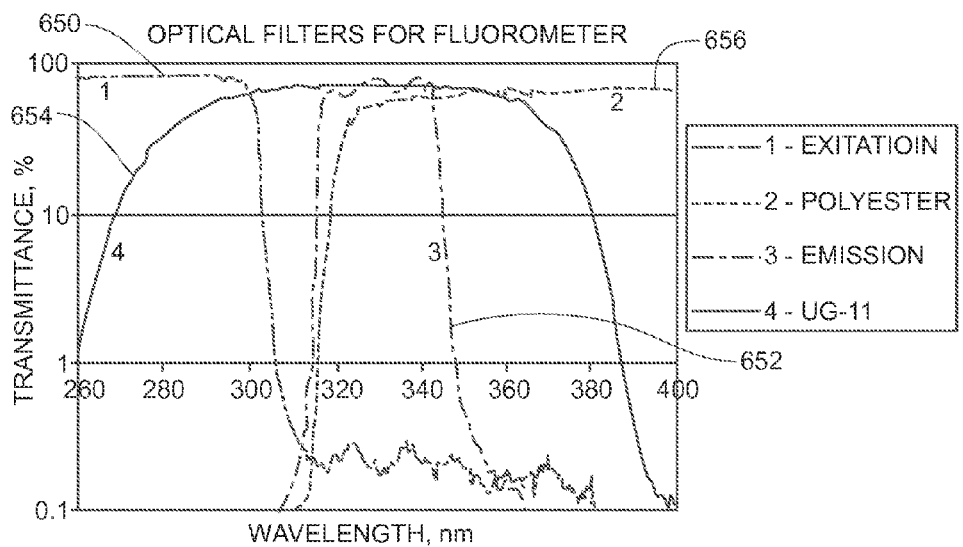
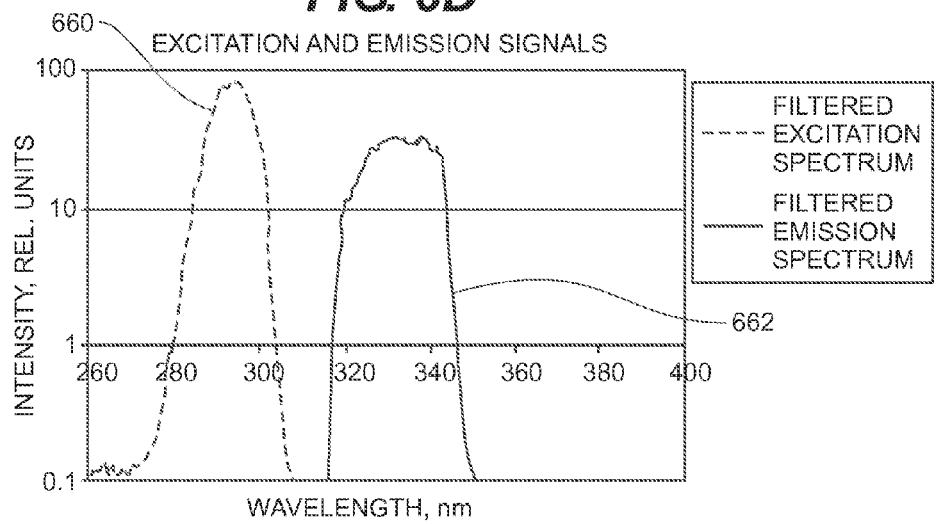

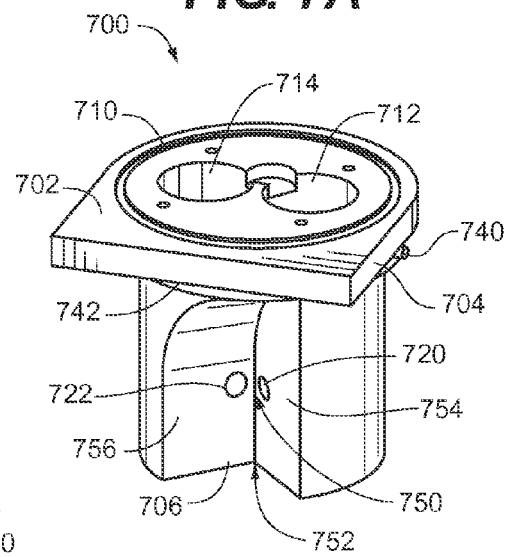
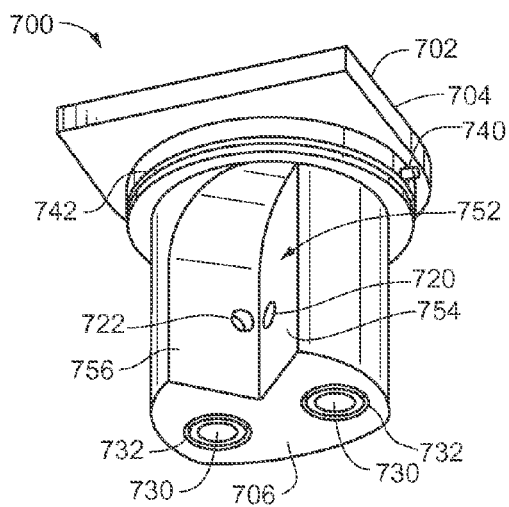
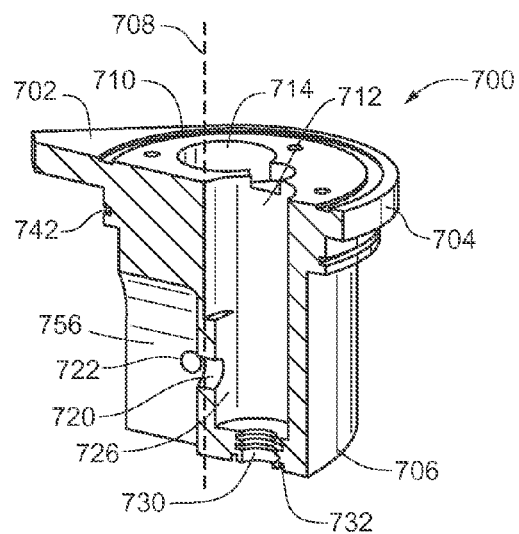

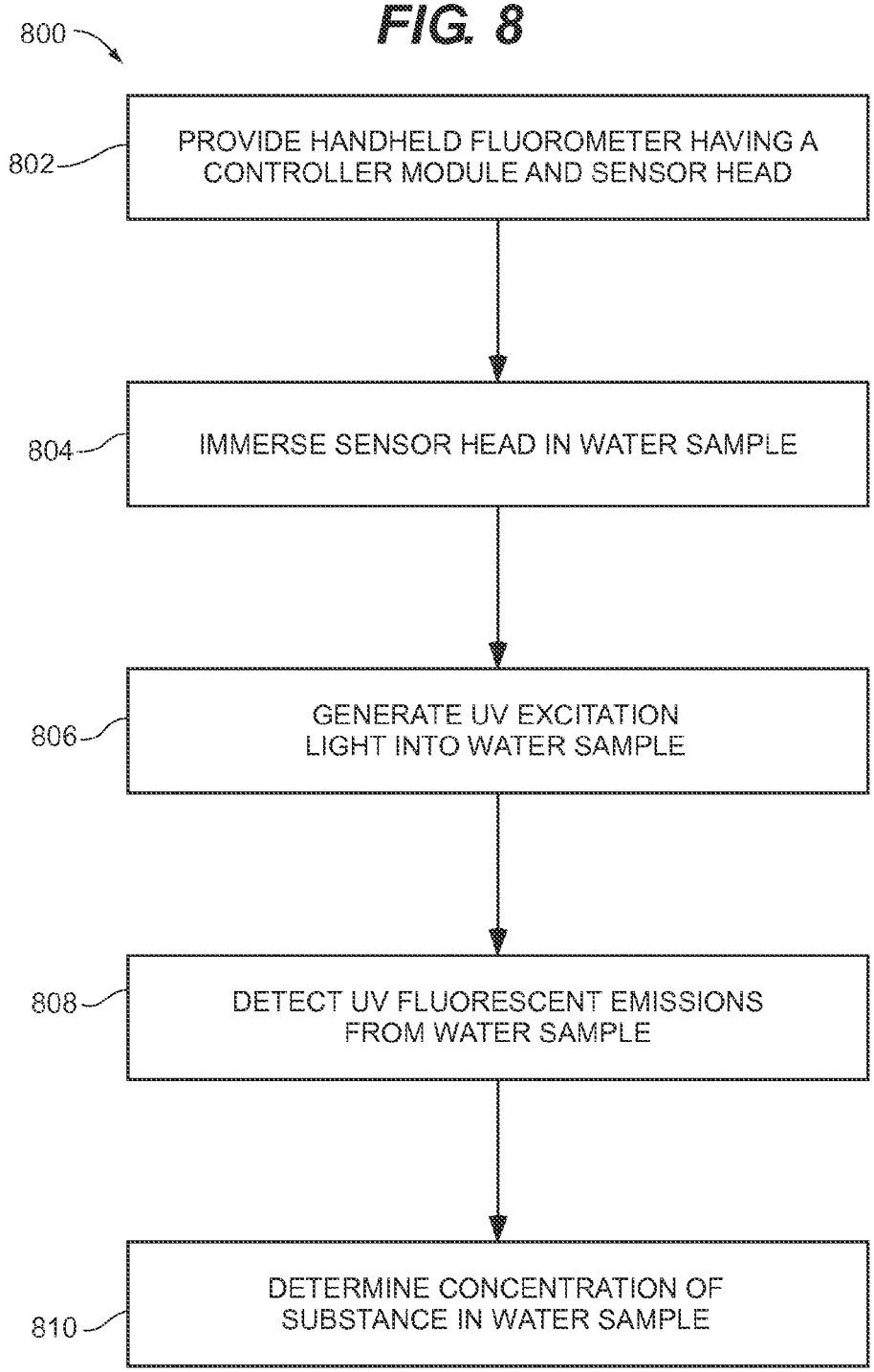

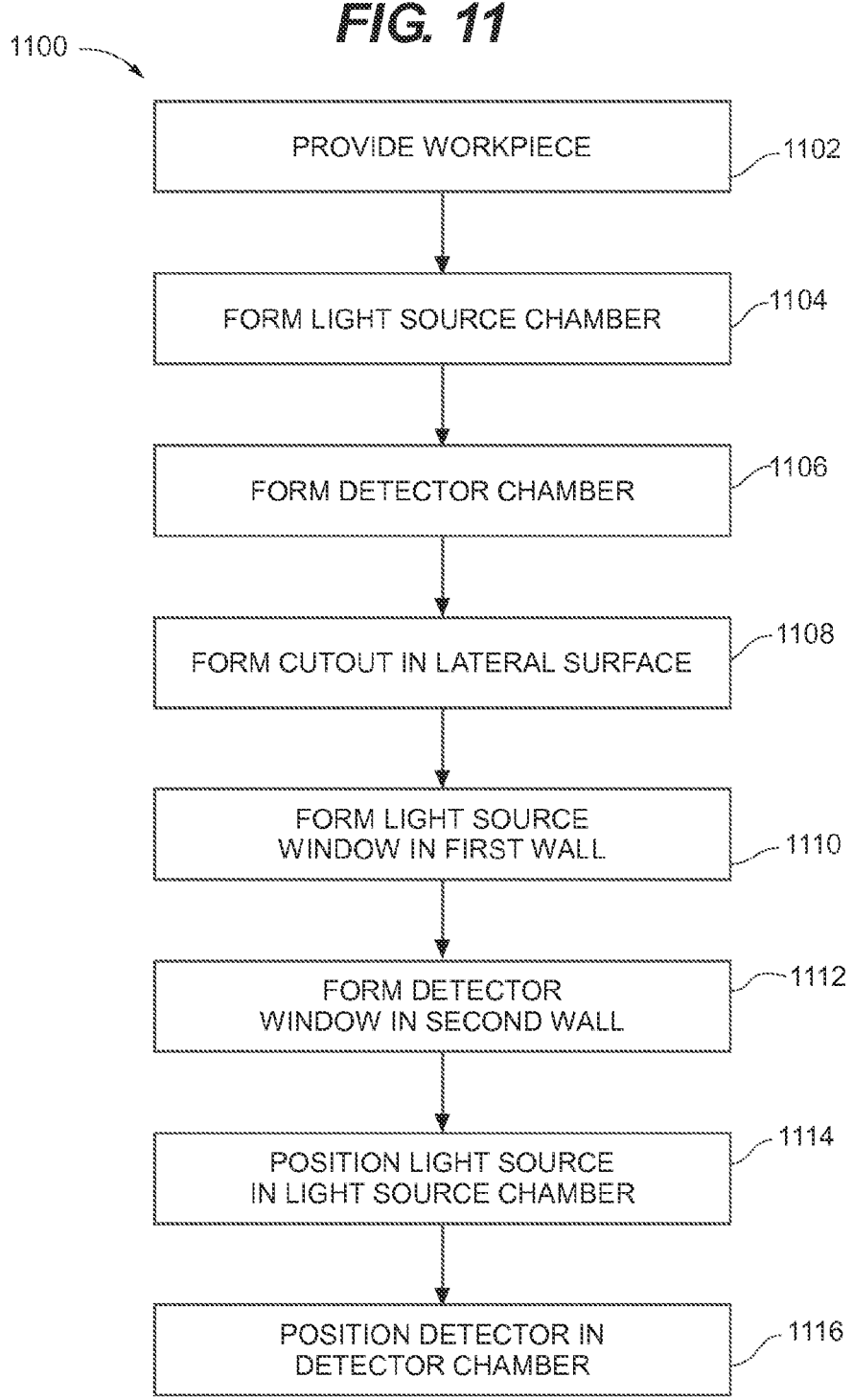

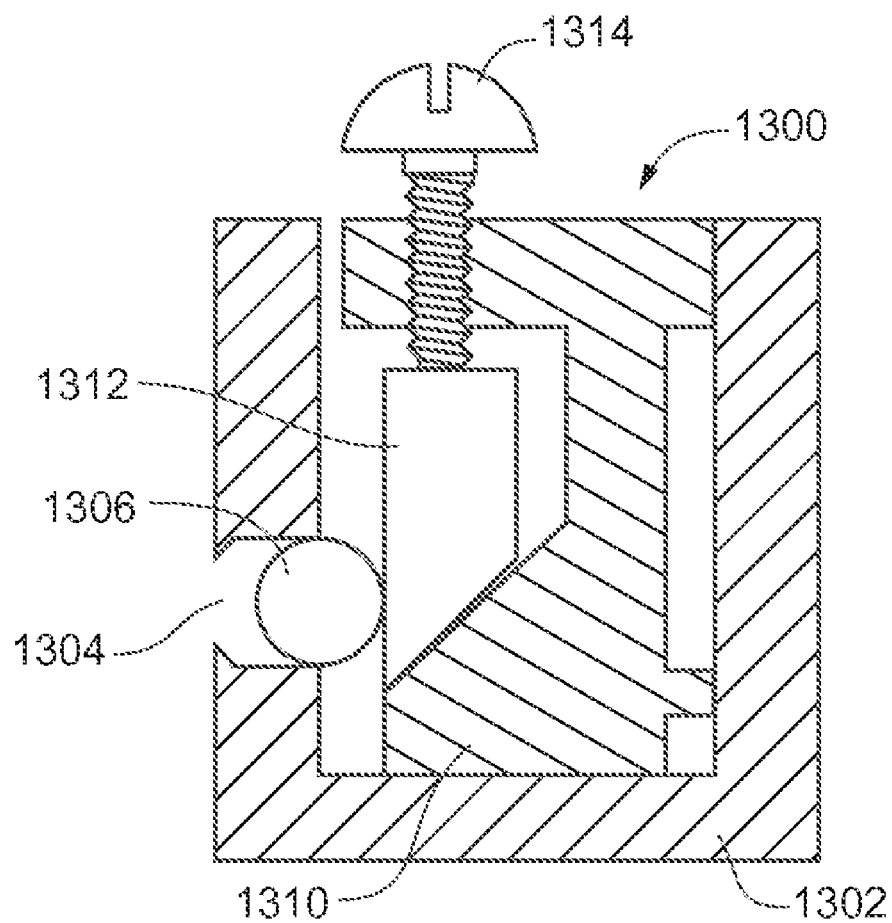

FLUOROMETRIC SENSOR

BACKGROUND

Embodiments of the present invention generally relate to optical measuring devices for testing a liquid sample, and more particularly to fluorometric sensors and fluorometers for determining and monitoring the concentration of one or more substances in a liquid sample.

In cleaning and antimicrobial operations, commercial users (e.g., restaurants, hotels, food and beverage plants, grocery stores, etc.) rely upon the concentration of the cleaning or antimicrobial product to make the product work effectively. Failure of a cleaning or antimicrobial product to work effectively (due to concentration issues) can cause a commercial user to perceive the product as lower quality. End consumers may also perceive the commercial user as providing inferior services. In addition, commercial users may be investigated and/or sanctioned by government regulatory and health agencies. Accordingly, there is a need for a system that can determine if the concentration of a product is within a specified concentration range. The same may be true for other applications, such as water care, pest control, beverage and bottling operations, packaging operations, and the like.

One method of monitoring the concentration of a product relies on monitoring the fluorescence of the product that occurs when the sample (and the product within the sample) is exposed to a predetermined wavelength of light. For example, compounds within the product or a fluorescent tracer added to the product may fluoresce when exposed to certain wavelengths of light. The concentration of the product can then be determined using a fluorometer that measures the fluorescence of the compounds and calculates the concentration of the chemical based on the measured fluorescence.

Fluorometric spectroscopy concerns the detection of fluorescent light emitted by a sample of interest. It involves using a beam of light, usually ultraviolet (UV) light, that excites the electrons in molecules of certain compounds in the sample and causes them to emit light of a lower energy (i.e., to "fluoresce"). There are several types of fluorometers for measuring emitted fluorescence. Fluorometers generally have of a source of excitation radiant energy, an excitation wavelength selector, a sample cell to contain the sample material, an emission wavelength selector, a detector with signal processor and a readout device. Filter fluorometers use optical filters to isolate the incident light and fluorescent light. Spectrofluorometers use diffraction grating monochromators to isolate the incident light and fluorescent light.

SUMMARY

Some embodiments of the invention generally relate to various designs for a fluorometric sensor capable of emitting excitation light into a sample of interest and then detecting and measuring fluorescent emissions from the sample. Some embodiments of the fluorometric sensor include a sensor head coupled with a controller that receives the measured fluorescence and calculates a concentration of a product within the sample. The sensor head includes one or more windows that transmit light between the sample and electronics within the sensor head, and in some cases include one or more features that improve the efficiency of the sensor head.

According to one aspect of the invention, a fluorometric sensor is provided, including an immersible sensor head and a controller coupled to the sensor head and adapted to calculate a concentration of a chemical in a water sample based on detected fluorescent emissions. The sensor head includes a housing having a first wall with a planar first exterior surface and a second wall with a planar second exterior surface. The sensor head also includes a light source chamber and a detector chamber. An ultraviolet (UV) light source is positioned within the light source chamber and emits a first UV wavelength for excitation of a water sample within an analytical area proximate the sensor head. A UV detector is positioned within the detector chamber and detects fluorescent emissions at a second UV wavelength from the analytical area. The UV detector is coupled with the controller. The sensor head also includes a light source window positioned in the first wall that transmits the first UV wavelength from the light source chamber into the analytical area and a detector window positioned in the second wall that transmits the second UV wavelength from the analytical area into the detector chamber. The light source window includes a first channel extending through the first wall and a first ball lens positioned in the first channel. The first ball lens has a radius $R_1$ and the first channel has a nominal diameter less than $2R_1$ such that the first channel is deformed about the first ball lens. This secures the first ball lens within the first channel and creates a continuous impermeable seal about the first ball lens between the light source chamber and the analytical area. The detector window includes a second channel extending through the second wall and a second ball lens positioned in the second channel. The second ball lens has a radius $R_2$ and the second channel has a nominal diameter less than $2R_2$ such that the second channel is deformed about the second ball lens. This secures the second ball lens within the second channel and creates a continuous impermeable seal about the second ball lens between the detector chamber and the analytical area.

According to another aspect of the invention, a fluorometric sensor is provided including an immersible sensor head and a controller coupled to the sensor head and adapted to calculate a concentration of a chemical in a water sample based on detected fluorescent emissions. The sensor head includes a plastic housing having a cutout in a lateral surface of the housing. The cutout defines a first wall with a planar first exterior surface and a second wall with a planar second exterior surface that intersects the first exterior surface at a first angle from about 60 degrees to about 120 degree. The sensor head also includes a light source chamber and a detector chamber. An ultraviolet (UV) light source is positioned within the light source chamber and emits a first UV wavelength for excitation of a water sample within an analytical area proximate the sensor head. A UV detector is positioned within the detector chamber and detects fluorescent emissions at a second UV wavelength from the analytical area. The sensor head also includes a light source window positioned in the first wall that transmits the first UV wavelength from the light source chamber into the analytical area and a detector window positioned in the second wall that transmits the second UV wavelength from the analytical area into the detector chamber. The light source window includes a first channel extending through the first wall and a first ball lens positioned in the first channel. The first ball lens has a radius $R_1$ and the first channel has a nominal diameter less than $2R_1$ such that the first channel is deformed about the first ball lens. This secures the first ball lens within the first channel and creates a continuous impermeable seal about the first ball lens between the light source chamber and the analytical area. The detector window includes a second channel extending through the second wall and a second ball lens positioned in the second channel. The second ball lens has a radius $R_2$ and the second channel has a nominal diameter less than $2R_2$ such that the second channel is deformed about the second ball lens. This secures the second ball lens within the second channel and creates a continuous impermeable seal about the second ball lens between the detector chamber and the analytical area. An axis of the second channel crosses an axis of the first channel at an intersect point in the analytical area. In some cases a first distance from the intersect point to the first exterior surface is from about $R_1$ to about $3R_1$, a second distance from the intersect point to the second exterior surface is from about $R_2$ to about $3R_2$, a third distance from a center of the first ball lens to the intersect point is from about $1.2R_1$ to about $3.2R_1$, and a fourth distance from a center of the second ball lens to the intersect point is from about $1.2R_2$ to about $3.2R_2$.

According to another aspect of the invention, a method for making an immersible fluorometric sensor head is provided. The method includes providing a plastic workpiece and forming a light source chamber and a detector chamber in the workpiece. A cutout is also formed in a lateral surface of the workpiece. The cutout and the light source chamber define a first wall with a first exterior planar surface and the cutout and the detector chamber define a second wall with a second exterior planar surface. The first and the second exterior planar surfaces intersect at a first angle. The method also includes forming a light source window in the first wall and a detector window in the second wall. Forming the light source window includes forming a first channel extending through the first wall and positioning a first ball lens in the first channel. The first ball lens has a radius $R_1$ and the first channel has a nominal diameter less than $2R_1$. In some cases the first ball lens is positioned by pushing the first ball lens into the first channel from the light source chamber. The first channel deforms about the first ball lens to secure the first ball lens and create a continuous impermeable seal about the first ball lens between the light source chamber and an exterior of the sensor head. Forming the detector window includes forming a second channel extending through the second wall and positioning a second ball lens in the second channel. The second ball lens has a radius $R_2$ and the second channel has a nominal diameter less than $2R_2$. In some cases the second ball lens is positioned by pushing the second ball lens into the second channel from the detector chamber. This deforms the second channel about the second ball lens to secure the second ball lens and create a continuous impermeable seal about the second ball lens between the detector chamber and the exterior of the sensor head. The method further includes positioning an ultraviolet (UV) light source in the light source chamber and a UV detector in the detector chamber. The UV light source emits a first UV wavelength through the light source window for excitation of a water sample within an analytical area proximate the sensor head and the UV detector detects fluorescent emissions at a second UV wavelength through the detector window from the analytical area.

Embodiments of the present invention can provide one or more of the following features and/or advantages. Some embodiments provide a fluorometer sensor head with improved sensitivity by, e.g., incorporating an efficient micro optics configuration to measure fluorescent signals at an angle (e.g., 60-120 degrees) to the direction of the excitation beam. In some embodiments, micro optic elements are arranged to bring an analytical area where fluorescent signals are measured closer to the focusing ball lenses. The shorter distance can greatly increase the efficiency and/or sensitivity of the sensor head. In some embodiments the analytical distance can be 5 to 10 times shorter than in previous designs. In some embodiments the analytical distance may be about 2 mm.

These and various other features and advantages will be apparent from a reading of the following detailed description.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

FIG. 6B is a cross-sectional view of a portion of an emission detector board according to some embodiments of the invention.

FIG. 6C is a plot showing examples of filter spectral transmissions according to some embodiments of the invention.

FIG. 6D is a plot showing a spectral separation between a filtered excitation spectrum and a filtered emission spectrum according to some embodiments of the invention.

FIG. 7A is a top perspective view of a sensor head according to some embodiments of the invention.

FIG. 7B is a bottom perspective view of the sensor head of FIG. 7A.

FIG. 7C is a perspective, cross-sectional view of the sensor head of FIG. 7A.

FIG. 8 is a flow diagram depicting a method for determining a concentration of a substance in a water sample according to some embodiments of the invention.

FIG. 11 is a flow diagram illustrating a method of making a sensor head according to some embodiments of the invention.

FIG. 13A is a cross-sectional view of a sensor head chamber and a positioning tool for positioning a ball lens according to some embodiments of the invention.

DETAILED DESCRIPTION OF THE PREFERRED EMBODIMENTS

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Embodiments of the invention generally provide a handheld optical measuring device having an immersible sensor head and methods of using such a device. In some embodiments components of the handheld optical measuring device are advantageously self-contained in a handheld configuration, providing a convenient tool for a variety of uses. In some embodiments of the invention, an optical measuring device in the form of a handheld fluorometer is provided. While some embodiments of the invention are described herein with reference to a fluorometer (handheld or otherwise), it should be understood that aspects of the invention can be embodied in a variety of optical measuring devices (e.g., turbidimeter, optical absorbance meter, etc.) and the invention is not limited to any particular form of device.

Figure 1:
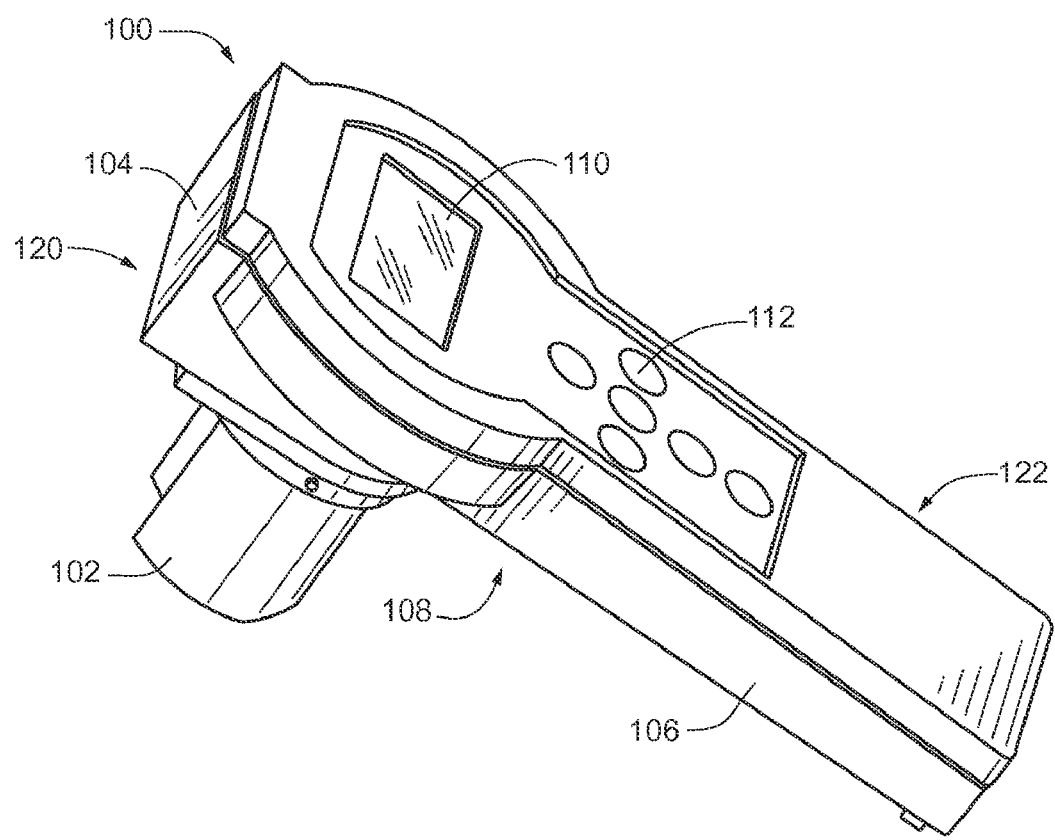
FIG. 1 is a perspective view of a handheld fluorometer according to some embodiments of the invention.

FIG. 1 is a perspective view of an optical measuring device in the form of a handheld fluorometer 100 according to some embodiments of the invention. The fluorometer 100 generally includes an immersible sensor head 102 connected to a handheld controller module 104. The controller module 104 also includes an electronic display 110 for displaying sensor readings and calculations to a user, and an input interface in the form of a keypad 112 that allows the user to interact with the fluorometer 100 (e.g., entering variables, setting parameters, accessing menu items, etc.).

According to some embodiments, the controller module 104 has a generally elongated housing 106 which provides a convenient form, similar to a handle or wand, to easily grasp or hold the fluorometer 100 by the hand. The sensor head 102 preferably includes a water-tight housing that enables it to take measurements and otherwise function when partially or wholly immersed in a liquid sample of interest. Accordingly, in some cases the sensor head 102 has some features and/or characteristics similar to an immersible dip probe. For example, in some embodiments of the invention the immersible sensor head 102 has one or more features and/or components similar to those described in commonly-assigned U.S. Pat. No. 7,550,746 and U.S. Patent Application Publication 2009/0212236, the entire contents of each of which is hereby incorporated herein by reference. The configuration of the immersible sensor head 102 can also be contrasted in some ways with fluorometers and other optical instruments that position sensors and other components exterior to an optical cell containing the sample of interest.

In some cases the sensor head 102 is connected to (e.g., attached to or integral with) a bottom surface 108 of the controller housing 106 opposite from the display 110 and positioned proximate a distal end 120 of the controller housing. In a typical fashion, a user can grasp the controller housing 106 near a proximal end 122 of the controller housing to take measurements from a sample, read the display 110, and/or manipulate the keypad 112. For example, a user may dip the sensor head 102 into a sample by holding the controller module 104 above the surface of a liquid sample (e.g., in a reservoir/container in the field, a beaker in the laboratory, etc.) with the sensor head 102 partially or completely immersed in the sample. In some embodiments, a user may grasp the second end of the controller module 104 while securing a sample cup filled with a sample about the immersible sensor head 102. Of course other configurations of the controller module and the sensor head are possible and the invention is not limited to any particular physical configuration.

In general, the handheld fluorometer 100 at minimum measures fluorescent emissions from a sample including a substance of interest (e.g., a chemical solution, such as an antimicrobial or cleaning product), calculates a concentration of the substance in the sample, and displays the determined concentration to a user. The user can then optionally perform any desired actions based on the determined concentration, such as, for example, adding more of the substance to an industrial system in order to increase the concentration of the substance. In this way, the fluorometer can be part of a manual feedback loop. If the fluorometer determines that the concentration is lower or higher than a threshold concentration, a user will see the difference and can adjust the product dispensation appropriately by either dispensing more or less product. Additionally, the fluorometer can function as part of an out-of-product alarm. When a product runs out, the fluorescence (which reflects the concentration of the product) will drop below a pre-determined threshold level. At this point, the sensor can alert a user that the dispenser is out of product. The signal can be a visual or audio signal, or a vibrating signal. Accordingly, such feedback will ensure that enough cleaner, antimicrobial or other composition is present to achieve the desired effect (cleanliness, reduction in microorganisms, lubrication, etc.).

The basic operation of fluorometers is well known, and accordingly, various details are omitted here for conciseness and clarity. In general, the fluorometer 100 calculates a concentration of a particular substance in a liquid sample based on fluorescent properties of the substance. As will be described in more detail herein, the fluorometer 100 includes a light source that emits light within a selected wavelength range. When the sensor head 102 is immersed in the liquid sample, the light encounters particles of the substance of interest, which excites the electrons in certain molecules of the substance and causes them to emit light of a lower energy (i.e., to "fluoresce") in another wavelength range. The sensor head 102 includes an optical sensor, such as a photodetector, that detects the fluorescent emissions and generates a corresponding electrical signal indicating the intensity of the fluorescent emissions. The fluorometer 100 includes a controller, coupled with the optical sensor, that can then calculate the concentration of the substance based on a known relationship between the intensity of the fluorescent emissions and the concentration of the substance.

A number of variations and specific details of this general process are contemplated for embodiments of the invention involving fluorometers. For example, the substance of interest may be any desired chemical solution having fluorescent properties. Examples include, but are not limited to, biocides such as pesticide and antimicrobial products, anticorrosion, antiscaling, and antifouling products, disinfectants, and other cleaning products, detergents, additives, and the like. For convenience, these and other such substances are alternately referred to herein simply as "products," "chemical solutions," and/or "treatment solutions." In addition, although examples are presented herein involving determining the concentration of water treatment solution(s) within a sample of cooling water (e.g., a water sample) used in various industrial systems (e.g., a cooling tower), it should be appreciated that the handheld fluorometer 100 may be useful in determining the concentration(s) of products in numerous settings to treat water and other liquids. As just a few examples, the handheld fluorometer 100 may be useful for determining concentrations of one or more substances in laundry, automatic warewashing, manual ware-washing, 3$^{rd}$ sink applications, power sink applications, vehicle care, clean-in-place operations, healthcare applications, hard surface applications and the like.

Many products fluoresce in the presence of light radiating from the sensor head 102 because many of the compounds that make up the products have fluorescent characteristics. For example, a compound or molecule that has a benzene component can incorporate one or more substituent electron donating groups such as —OH, —NH$_2$, and —OCH$_3$, and polycyclic compounds that exhibit fluorescent characteristics. Many compounds used in the above-described applications include chemical structures like these, such as surfactants, lubricants, antimicrobial agents, solvents, hydrotropes, antiredeposition agents, dyes, corrosion inhibitors and bleaching additives. These compounds can be incorporated into products like ware-washing detergents, rinse aids, laundry detergents, clean-in-place cleaners, antimicrobials, floor coatings, meat, poultry and seafood carcass treatments, pesticides, vehicle care compositions, water care compositions, pool and spa compositions, aseptic packaging compositions, bottle washing compositions, and the like. Examples of some of these compounds and corresponding applications can be found in U.S. Pat. No. 7,550,746, the entire content of which is herein incorporated by reference.

Additionally, or alternatively, fluorescent tracers (also referred to herein as "fluorescent markers") can be incorporated into products that may or may not already include naturally fluorescing compounds. Some non-limiting examples of tracers include naphthalene disulfonate (NDSA), 2-naphthalenesulfonic acid, Acid Yellow 7,1,3,6,8-pyrenetetrasulfonic acid sodium salt, and fluorescein. In some embodiments the fluorescent tracer is added to the product in a known proportion, thus making it possible to estimate the concentration of the product once the concentration of the tracer is determined. For example, in some cases the concentration of the fluorescent tracer can be determined by comparing a current fluorescent signal with fluorescent signals from known tracer concentrations measured during a calibration procedure. The concentration of chemical product can then be estimated from the known nominal proportion of fluorescent tracer and measured concentration of fluorescent tracer. In some cases a current concentration of a product, $C_c$, in a liquid sample can be determined by $$C_c = C_m \times (C_0/C_f), \text{ wherein}$$

$$C_m = K_m \times (S_x - Z_0), \text{ and}$$

wherein $C_m$ is a current fluorescent marker concentration, $K_m$ is a slope correction coefficient, $S_x$ is a current fluorescent measurement, $Z_0$ is a zero shift, $C_0$ is a nominal concentration of the product, and $C_f$ is a nominal concentration of the fluorescent tracer.

Figure 2:
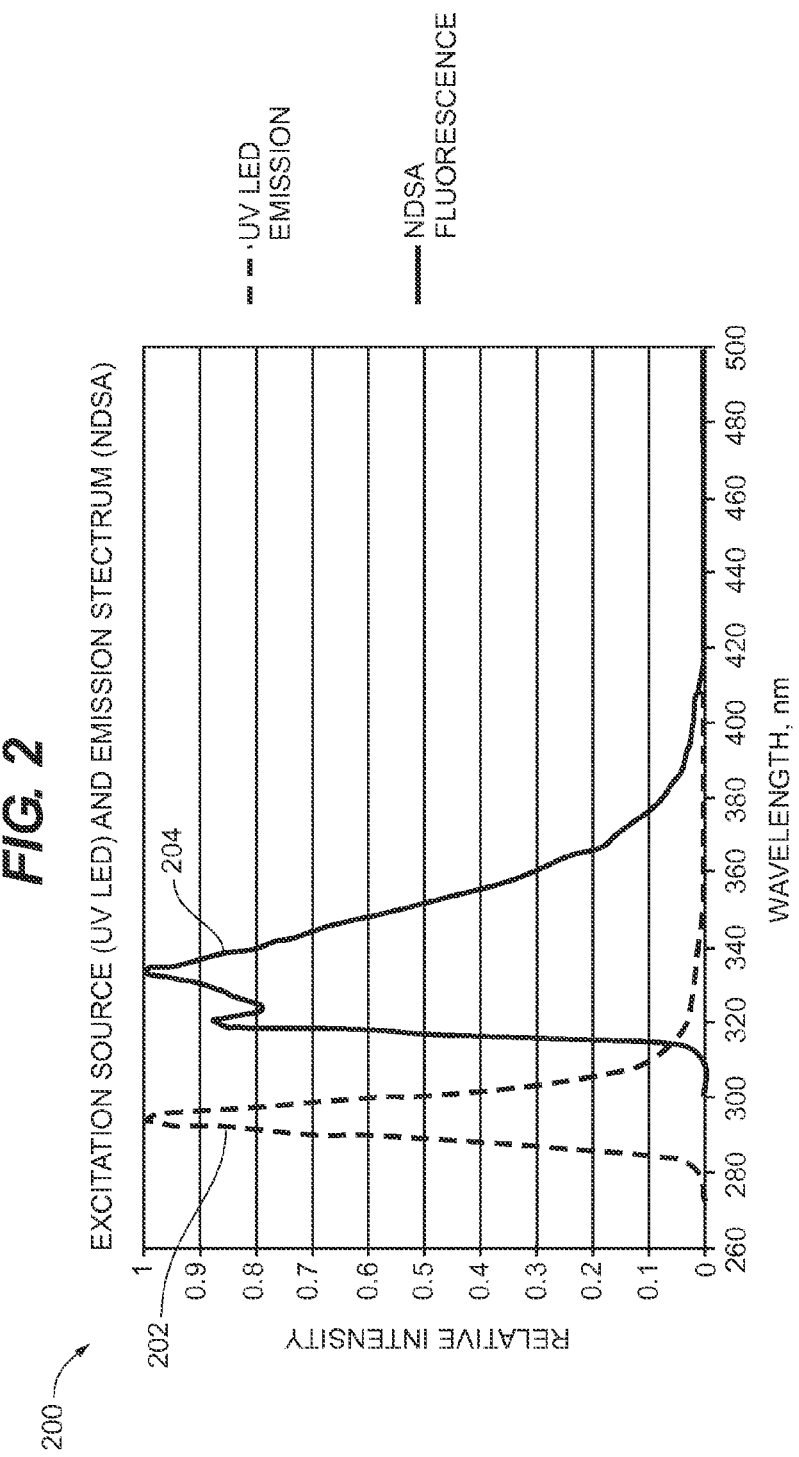
FIG. 2 is a plot of excitation and emission spectrum intensity according to some embodiments of the invention.

Referring to FIG. 2, a plot 200 is shown of an excitation spectrum intensity 202 and an emission spectrum intensity 204 according to some embodiments of the invention. In this example, a fluorometer having a light source in the form of an ultra violet (UV) light emitting diode (LED) emits excitation light within a range from about 280 nm to about 310 nm into a sample of cooling tower water having a product with an added fluorescent tracer, NDSA. The added NDSA absorbs this UV radiation and produces fluorescence in a range from about 310 nm to about 400 nm. The emission detector of the fluorometer detects this emitted radiation, and the fluorometer determines the concentration of the NDSA tracer, and ultimately the concentration of the product within the sample of the cooling tower water.

Figure 3:
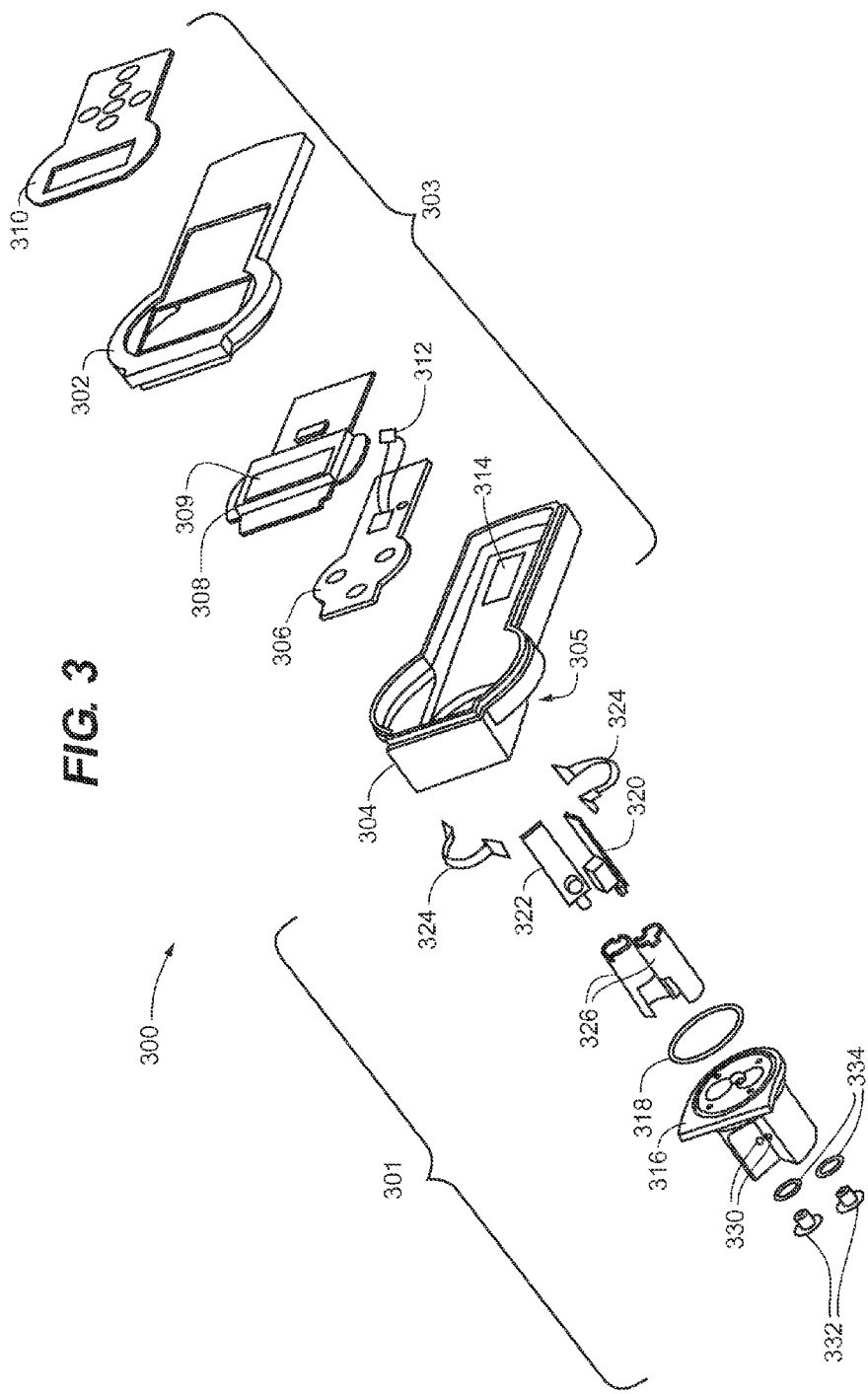
FIG. 3 is an exploded view of a handheld fluorometer according to some embodiments of the invention.

FIG. 3 is an exploded view of a handheld fluorometer 300 similar to the handheld fluorometer shown in FIG. 1. The fluorometer 300 generally includes an immersible sensor head 301 connected to a controller module portion 303. The controller module 303 includes a housing and several components within the housing. The housing is formed from a top portion 302 and a bottom portion 304, with the bottom portion 304 of the controller housing defining a bottom surface 305 on the exterior of the bottom portion. The sensor head 301 includes a sensor head housing 316 that is configured to be fixedly attached to the bottom surface 305 of the controller housing. In some embodiments the sensor head housing 316 may be integrally formed with one or more portions of the controller housing.

In some embodiments the controller module 303 generally includes those components necessary to determine a concentration of a product based on a signal received from the sensor head 301. As shown in FIG. 3, the controller module 303 includes a control board 306 that couples with a display board 308 via a display board cable 312. The display board 308 includes an electronic display 309 (e.g., an LCD screen) that displays information to a user. The controller module 303 also includes an input interface in the form of a membrane keypad overlay 310, which allows the user to enter a variety of information for use by the controller module 303. The controller module 303 also includes a portable power source, e.g., battery, 314 for powering the circuits within the fluorometer 300.

In some embodiments the immersible sensor head 301 has one or more features and/or components similar to those described in commonly-assigned U.S. Pat. No. 7,550,746 and U.S. Patent Application Publication 2009/0212236, the entire contents of each of which is hereby incorporated herein by reference. Referring back to FIG. 3, in some embodiments, the sensor head 301 includes a housing 316 that houses a light source board 320 and an emission detector board 322. A first O-ring 318 provides a seal between the sensor head housing 316 and the bottom portion 304 of the controller housing. The components on the light source board 320 and the emission detector board 322 are shielded by a brass tube 326 that substantially encircle each board. Each tube 326 includes a cutout at the distal end of the tube, and the sensor head housing 316 includes windows 330 extending through the housing. These cutouts and the windows 330 allow a light source (e.g., LED) positioned on the light source board 320 and an emission detector (e.g., photodetector) positioned on the emission detector board 322 to communication with an analytical area outside the sensor head housing 316. Electrical cables 324 couple the light source board 320 and the emission detector board 322 to the control board 306, which allows the controller on the board 306 to control the light source and receive signals back from the emission detector. In some embodiments the sensor head 301 also includes one or more temperature sensors that are able to measure the temperature of a water sample. For example, the light source board 320 and/or the emission detector board 322 may include one or more temperature sensors that extend into the sensor head housing 316. Covers 332 positioned in a distal face of the sensor housing 316, along with additional O-rings 334, provide a seal around the temperature sensors.

Figure 4:
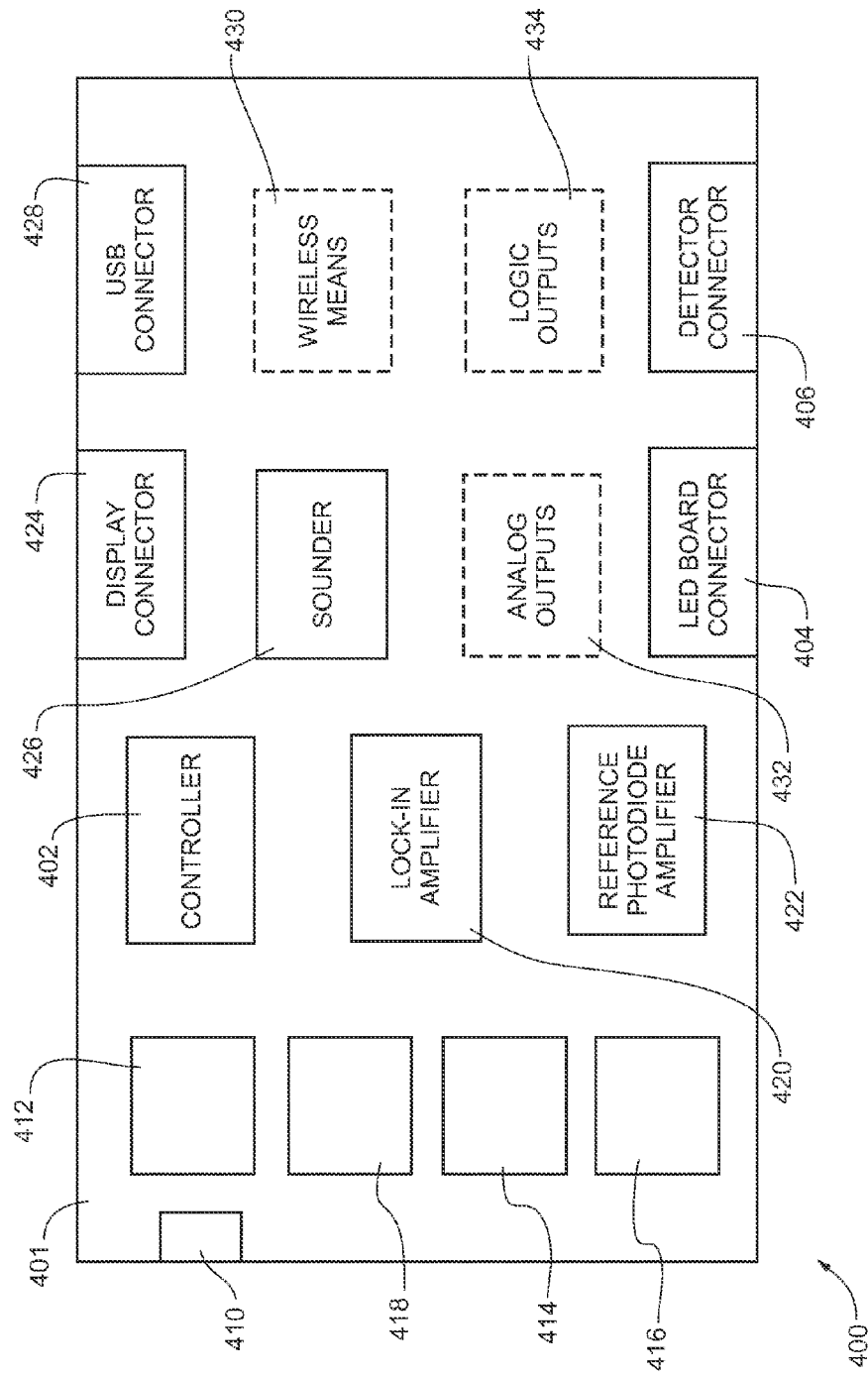
FIG. 4 is a schematic diagram of a controller board according to some embodiments of the invention.

FIG. 4 is a schematic diagram of a controller board 400 for a handheld fluorometer according to some embodiments of the invention. The controller board 400 can comprise a number of discrete components positioned (e.g., soldered) and coupled together (connections not shown) on a printed circuit board 401. FIG. 4 presents a simplified schematic of the basic components of one exemplary control board 400, and it will be appreciated by those skilled in the art that various connections between the components and/or details about components may vary. The control board 400 includes a controller 402, which calculates a concentration of a product within a water sample based on an intensity signal from the emission detector. The controller 402 may provide a variety of other functions, including without limitation, performing a calibration routine, accepting and executing instructions entered at the input interface, and/or formatting data for viewing on the fluorometer's display. The controller 402 can be embodied in any suitable form, such as a software driven microprocessor, a microcontroller, or a field programmable gate array, or a fixed hardware design such as an application specific integrated circuit, etc. In addition, the controller 402 may have onboard memory, or the control board may have memory (not shown) that stores instructions for execution by the controller 402.

The control board also includes a power cable with a connector 410 for connecting the board 400 to a power source such as the battery 314 shown in FIG. 3. The board 400 also includes a controller power supply 412, an analog power supply 414, and a light source power supply 416 for powering the light source in the sensor head. In some embodiments the control board 400 includes a real-time clock battery 418, a lock-in amplifier 420, a reference photodiode amplifier 422, and connectors for the display board 424, the light source board 404, and the emission detector board 406. In some cases, the control board 400 may also have a sounder 426, a USB or other type of data connector 428, wireless means 430 for communicating with other computing devices, and optional analog 432 and logical 434 outputs.

Figure 5A:
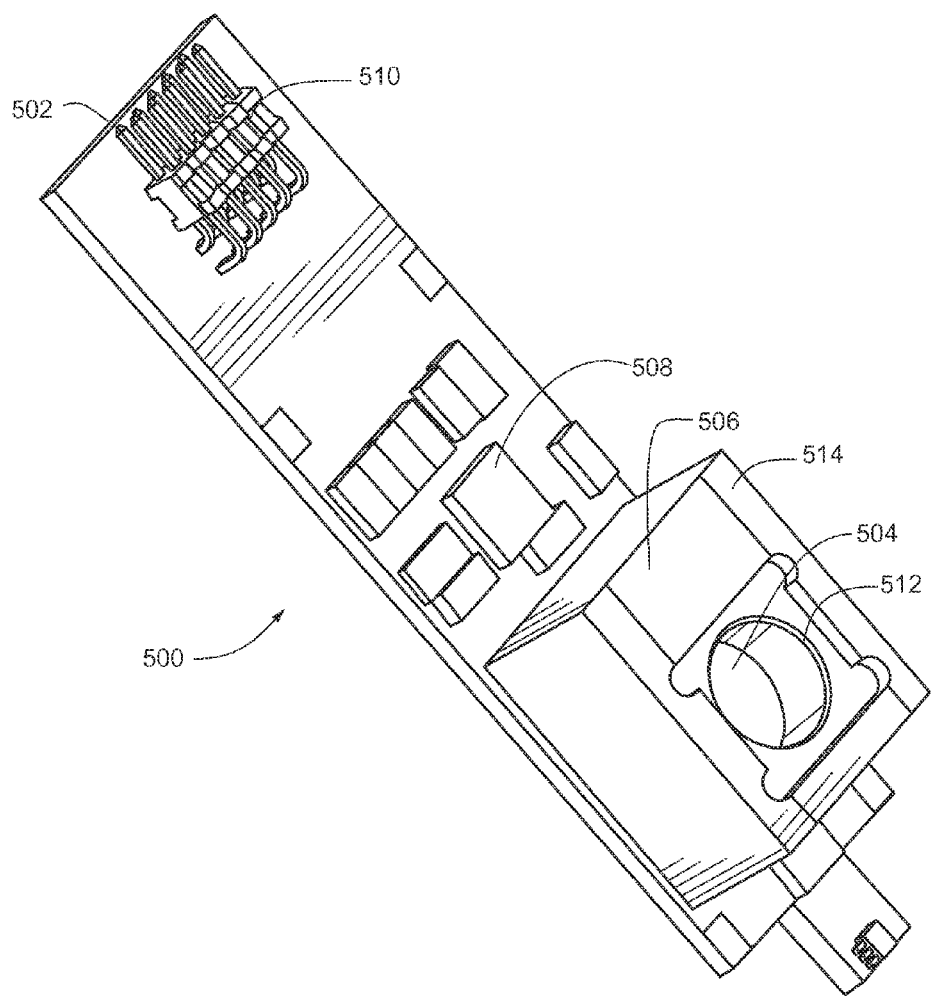
FIG. 5A is a perspective view of a light source board according to some embodiments of the invention.
Figure 5B:
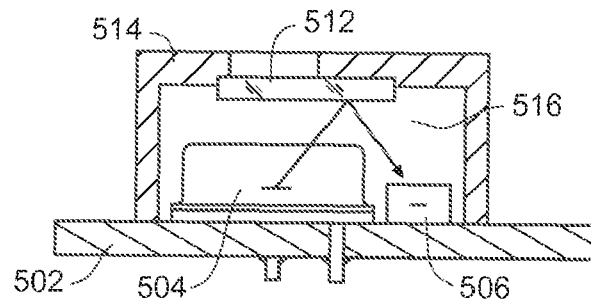
FIG. 5B is a cross-sectional view of a portion of a light source board according to some embodiments of the invention.

FIG. 5A is a perspective view of a light source board 500 according to some embodiments of the invention. The board 500 (also shown in FIG. 3 as 320) generally includes a printed circuit board 502 having a light source 504 and a reference photodiode 506, along with a preamplifier 508 and a connector 510 for coupling the board 500 with the control board. FIG. 5B is a cross sectional view showing one embodiment in which the light source 504 and the reference photodiode 506 are inside an optical cavity 516 formed by a filter holder 514 secured on the printed board 502. A small portion of light from the light source 504 reaches the reference photodiode 506, providing a reference signal to compensate for variations in light source output intensity with time and with variations of temperature. In some cases the reference signal is produced by reflection from an excitation filter 512 and scattering light inside of cavity 516. In some cases the reference signal is stable and proportional to the total output of the light source 504. In some embodiments the reference photodiode 506 works without optical attenuators or beam splitters because of natural attenuation of light in the optical cavity 516. The excitation filter 512 is positioned by the filter holder 514 over the light source 504, to filter the light from the light source 504 before it leaves the immersible sensor head. The light source 504 can include a variety of possible elements. For example, light source 504 may be a gas discharge lamp, a mercury lamp, a deuterium lamp, a metal vapor lamp, a light emitting diode (LED) or a plurality of LEDS. In addition, the light source 504 may emit excitation radiation in a number of possible spectrums depending upon the element chosen and the spectrum desired. In some embodiments the light source is an ultraviolet LED, capable of emitting light having a wavelength from about 280 nm to about 310 nm.

Figure 5C:
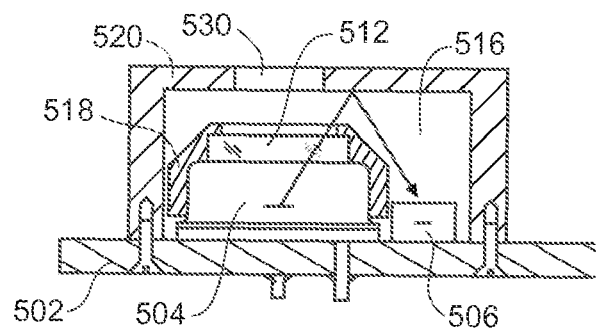
FIG. 5C is a cross-sectional view of a portion of a light source board according to some embodiments of the invention.

FIG. 5C shows another embodiment of the optical cavity 516. An excitation filter 512 is secured directly on the top of UV LED 504. A cover 520 creates an optical cavity 516 around the UV LED and the reference photodiode 506. The cover 520 has an exit opening 530 to couple the UV LED with an excitation window (for example one window 330 as shown on FIG. 3). In some cases a main portion of the UV light emitted by the UV LED travels from UV LED 504 through the exit opening 530 to the excitation window. In some cases a smaller portion of the UV light is reflected and scattered inside of the optical cavity 516, providing a stable reference signal proportional to UV LED intensity. In some embodiments the cover 520 and/or a filter holder 518 are made of polytetrafluoroethylene to improve the intensity of scattered signals and a long term stability of the reference signal. In some embodiments the cover 520 can have a polished internal surface with a metallized reflective layer and/or the filter holder 518 has a polished external surface with a metallized reflective layer to improve the intensity of reflected signals and stability of the reference signal.

Figure 6A:
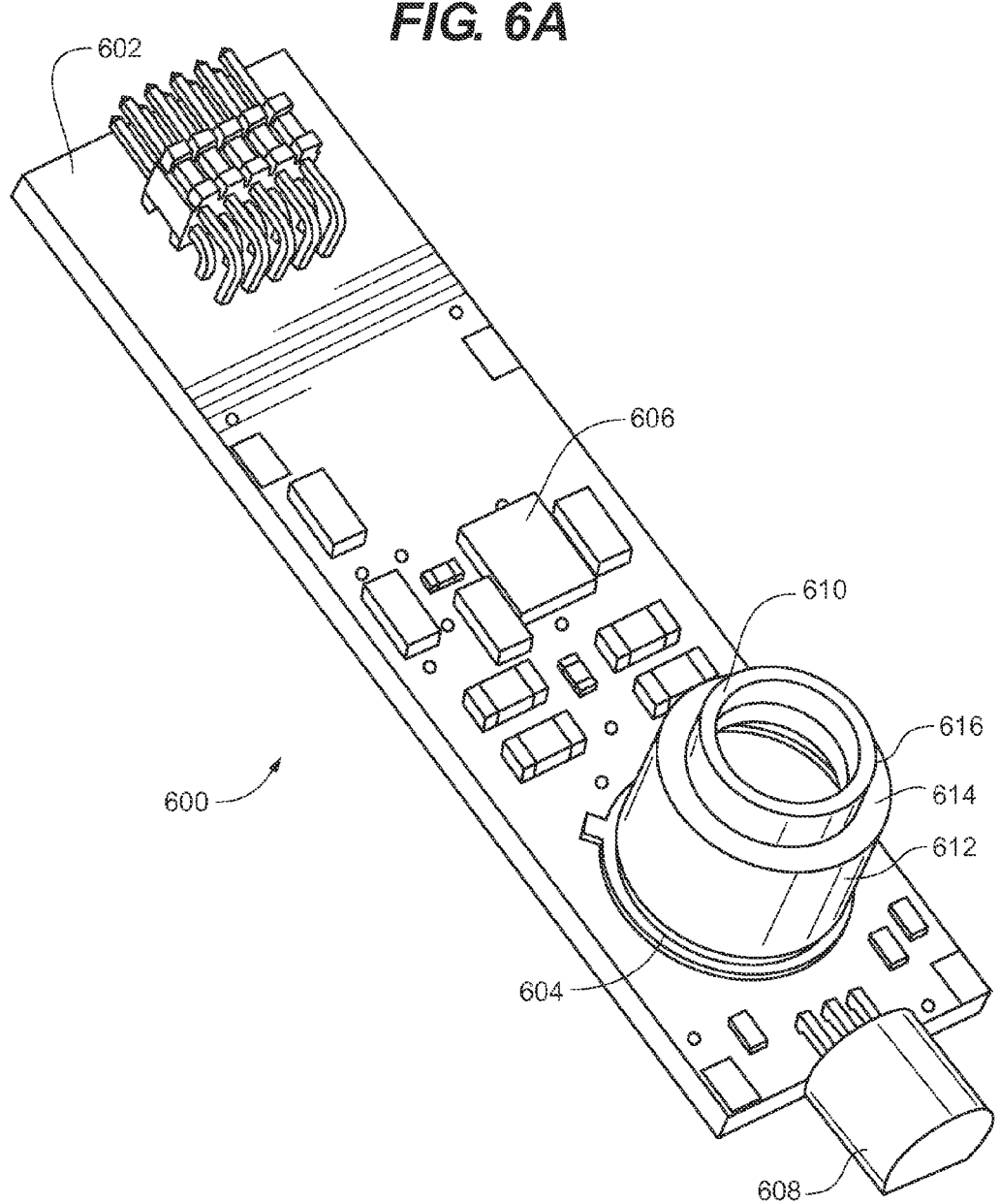
FIG. 6A is a perspective view of an emission detector board according to some embodiments of the invention.

FIGS. 6A and 6B show an emission detector board 600 according to some embodiments of the invention. FIG. 6A is a perspective view of the emission detector board 600. The detector board 600 generally includes a number of components, including an emission detector 604 positioned on a printed circuit board 602. In some embodiments of the invention, the emission detector 604 comprises a UV-sensitive photodiode. For example, the detector 604 may generate an intensity signal based on light from about 310 nm to about 400 nm that it detects from an analytical area outside the sensor head. The detector board 600 also includes a preamplifier 606 and a temperature sensor 608. An emission filter holder 610 positioned about the emission detector 604 supports one or more filters for screening the radiant energy and passing on the desired wavelengths to the detector 604. In the embodiment shown in FIG. 6B, the filters include an interference filter 612 and a UG-11 glass filter 614. In some embodiments, an additional polyester film filter 616 is also positioned in front of the emission detector 604. In some cases the polyester film filter 616 has a thickness of about 0.5+/−0.2 mm. In some cases optical designs can provide increased optical efficiency (e.g., using ball lenses, highly divergent beams, etc.) but may also compromise the performance of interference filters which have a high efficiency and a high rejection value for collimated beams. Incorporating such a polyester film can in some cases minimize stray light levels to allow measurements of NDSA fluorescence in samples with a turbidity as high as 100 Nephelometric Turbidity Units (NTU).

FIG. 6C is a plot showing examples of a spectral transmission 650 of the excitation filter 512, a spectral transmission 652 of the interference filter 612, a spectral transmission 654 of the UG-11 glass filter 614 and a spectral transmission 656 of the polyester film filter 616 according to some embodiments of the invention. In some embodiments this combination of filters provides an efficient spectral separation between the excitation light spectrum from the UV LED and the emission light spectrum from the fluorescent tracer within the sample. FIG. 6D is a plot showing the spectral separation between a filtered excitation spectrum 660 and a filtered emission spectrum 662 utilizing the excitation filter 512, the interference filter 612, the UG-11 glass filter 614 and the polyester film filter 616.

FIGS. 7A-7C present various views of a discrete immersible sensor head 700 according to some embodiments of the invention that can be attached to a controller module of a handheld fluorometer such as of those previously discussed. FIG. 7A is a top perspective view of the sensor head 700, FIG. 7B is a bottom perspective view of the sensor head 700, and FIG. 7C is a perspective, cross-sectional view of the sensor head 700. The sensor head 700 can be made from a plastic and may be molded and/or milled to achieve the desired shape and features.

In general, the sensor head 700 comprises a housing 702 that includes a first vertical cavity or chamber 712 that is configured to receive a light source circuit board (e.g., the light source board 320 of FIG. 3 or 500 of FIG. 5). In some cases the light source chamber 712 is formed with a cylindrical configuration, which can provide a snug fit for the cylindrical brass shields 326 illustrated in FIG. 3. In some embodiments the light source chamber 712 has a partially-cylindrical configuration including a planar wall 726 along one lateral side of the chamber 712. Returning to FIGS. 7A-7C, the sensor head housing 702 includes a second vertical cavity or chamber 714 for receiving an emission detector circuit board (e.g., the emission detector board 322 of FIG. 3 or 600 of FIG. 6), similar to the light source chamber 712. In some cases the light source chamber 712 and the emission detector chamber 714 may be formed and positioned symmetrically about a longitudinal axis 708 of the sensor head 700, although this is not required in all embodiments.

The sensor head housing 702 further includes an angular cutout 752 in the exterior surface of the housing 702. In some embodiments the angle of the cutout 752 is approximately 90 degrees, although it should be understood that the invention is not limited to a particular angle for the cutout. The cutout 752 is bounded by a first wall 754 intersecting a second wall 756 at the longitudinal axis of the sensor head 700. The first wall 754 defines a light source window 720 that provides a path through the first wall 754 for excitation energy emitted by the light source. The second wall 756 similarly defines a emission detector window 722 that provides a path through the second wall 756 for fluorescent emissions to reach the emission detector located within the sensor head housing 702. In some embodiments, the light source window 720 and/or the emission detector window 722 comprise a channel extending through the sensor head housing 702. In some embodiments the windows 720, 722 also include a lens, prism or other material optically transparent to the light source radiation and/or fluorescent emissions. For example, in some embodiments a glass or sapphire ball lens is positioned within each channel. Other suitable materials known in the art may also be used. The ball lens provides the light source/detector window, but also provides a focusing means for directing light between the light source/detector and an analytical area 750 outside the housing 702 of the sensor head 700.

As shown in the figures herein, the angular cutout 752, including the light source window 720 and the emission detector window 722, are oriented with respect to the controller module such that the angular cutout and the windows face toward the distal end of the controller module. As discussed further herein, the angular cutout and the windows may be oriented in a different direction in some embodiments. For example, in some embodiments the angular cutout and the windows face toward the proximal end of the controller module.

In some embodiments, the sensor head 700 includes a proximal end 704 and a distal end 706, between which extends the longitudinal axis 708 and a length of the sensor head 700. As shown in FIGS. 1 and 3, in some embodiments the sensor head 700 is connected to the bottom surface of the controller module housing at or near the proximal end 704 of the sensor head 700. In some cases the sensor head 700 may be fixedly attached to the controller housing with a fastener. The fastener can include, but is not limited to, screws, bolts, and/or pins, or an adhesive or weld (not shown in the figures). In some embodiments the sensor head 700 is secured with four screws that compress an O-ring positioned in a groove 710 between the sensor head 700 and the controller module. In some embodiments, the sensor head housing 702 may be integrally formed with the controller module such that there is a seamless transition between the proximal end 704 of the sensor head and the bottom surface of the controller module.

In some embodiments the sensor head 700 also includes part or all of a fastener that removably fastens a sample cup about the sensor head 700. As just one example, the fastener may comprise one or more pins 740 positioned about the sensor head housing 702 and corresponding slots on the sample cup. In some embodiments the pins 740 and the slots form a bayonet fastener that secures the sample cup about the sensor head and also aligns the sample cup in a preferred orientation (e.g., rotation) about the sensor head 700. Other fasteners (e.g., screw threads, opposing pressure elements, etc.) can also be included.

In some embodiments the sensor head 700 also includes holes 730 for inserting one or more temperature sensor covers, such as those depicted in FIG. 3. Returning to FIGS. 7A-7C, the holes 730 may be threaded or otherwise configured to receive and secure the temperature sensors. The temperature sensors (not shown in FIGS. 7A-7C) are adapted to sense the current temperature of the water sample and generate a corresponding signal that can be used to correct concentration calculations based on errors due to, e.g., temperatures outside an acceptable range.

In addition, the sensor head 700 is preferably an immersible sensor head, meaning that it is partly or wholly immersed below the surface of a water sample when taking fluorescent emission measurements. Accordingly, the sensor head housing 702, connection to the controller housing, and any windows or other potential voids in the housing 702 are effectively sealed prior to immersion. For example, in some cases the housing 702 includes a first O-ring groove 710 at the proximal end 704 of the sensor head and second O-ring grooves 732 around the temperature sensor holes 730. In some embodiments including a sample cup, a third O-ring groove 742 may also be formed around the circumference of the sensor head 700 near the proximal end 704 of the sensor head in order to provide a substantially impermeable seal between the sample cup and the sensor head 700. In addition, the light source window 720 and emission detector window 722 may also be sealed with O-rings and the like. In some embodiments, the light source window 720 and emission detector window 722 are sealed due to a pressure fit between the window channels and the ball lenses placed within the channels.

FIG. 8 is a flow diagram depicting a method of determining a concentration of a product in a water sample according to some embodiments of the invention. In general, the fluorometer measures a fluorescent light emission of the active molecule in the product that is proportional to the actual concentration of the product in the water sample. After providing a handheld fluorometer having a controller module and a sensor head connected to the controller module (802), a water sample containing the product of interest is provided. The sensor head is immersed in the water sample (804) and the water sample occupies an analytical area of the sensor. Next, an ultraviolet (UV) excitation light having a first UV wavelength is generated by a light source in the sensor head and directed into the water sample and the analytical area (806).

The sensor head then detects and measures the fluorescent emissions of the sample at a second UV wavelength (808). The sensor head includes a controller (402 in FIG. 4, for example) that calculates the concentration of the product in the sample based on the measured fluorescent emissions (810). The first wavelength may be in the range of 280-310 nm. The second UV wavelength may be in the range of 310 nm to 400 nm. The sensor may also measure a reference fluorescence emission of the sample at the first wavelength. The sensor may also measure a fluorescence emission of a zero solution having zero concentration of the chemical. In that case, the concentration of the chemical in the sample may be calculated based on the calculated difference in the measured fluorescence emission of the sample containing the chemical and the measured fluorescence emission of the zero solution. The concentration of the sample may also be calculated based on a calibration constant determined for known concentrations of the product in a calibration sample.

As an example, in some cases sample concentrations may be evaluated based upon signals from two UV detectors. A reference detector measures an intensity of the UV excitation generated by the light source, while a fluorescent emission detector measures an intensity of the fluorescent emissions emitted by the product. The calculation uses the following equations:

$$C_C = K_X \left( \frac{I_E^S}{I_R^S} - \frac{I_E^0}{I_R^0} \right)$$

where $C_C$ is an actual, current concentration of a product X (for example, a surfactant, an antimicrobial agent, etc) in a sample solution;

$K_X$ is a calibration coefficient;

$I_E^S$ is an output signal from the emission detector for the sample solution;

$I_R^S$ is an output signal from the reference detector for the sample solution;

$I_E^0$ is an output signal from the emission detector for a zero solution (i.e., a solution with zero concentration of the product); and $I_R^0$ is an output signal from the reference detector for the zero solution.

$$K_X = C_{CALIBR} \bigg/ \left( \frac{I_E^{CALIBR}}{I_R^{CALIBR}} - \frac{I_E^0}{I_R^0} \right)$$

where $C_{CALIBR}$ is a concentration of the product in a calibration solution;

$I_E^{CALIBR}$ is an output signal from the emission detector for the calibration solution; and $I_R^{CALIBR}$ is an output signal from the reference detector for the calibration solution.

In some embodiments the fluorescent output signal is a nonlinear function of the product concentration. For example, a linearized current concentration, $C_L$, of a product X in a sample solution can be calculated using the following equation:

$$C_L = A \cdot R \cdot (1 + B \cdot R + C \cdot R^2 + D \cdot R^3)$$

where A, B, C, and D are linearization coefficients which can be found during calibration and $$R = \left( \frac{I_E^S}{I_R^S} - \frac{I_E^0}{I_R^0} \right)$$

is a ratio metric output signal based on emission and reference detector signals for a sample and a zero solution as described above herein.

In some embodiments the fluorescent output signal is a nonlinear function of temperature. For example, a temperature corrected concentration, $C_L^T$, of a product X in a sample solution can be calculated using the following equation:

$$C_L^T = C_L \cdot (1 + K_1(t_S - t_{CALIBR}) + K_2(t_S - t_{CALIBR})^2)$$

where $K_1$ and $K_2$ are temperature correction coefficients which can be found during calibration;

$t_S$ is a sample temperature during measurements; and $t_{CALIBR}$ is a sample temperature during calibration.

As discussed above with reference to FIG. 4, the controller 402 within the handheld fluorometer can calculate the concentration of the product in a sample based on the intensity signal from the emission detector. In some embodiments the controller 402 may also calculate the product concentration based on a calibration constant, zero shift, and/or an excitation reference signal using the relationships described above. Operation instructions for the controller may be stored in an onboard or discrete memory. In that respect, the memory may be a computer-readable medium comprising program instructions that cause the controller to provide any of the functionality ascribed to them, and perform any of the methods described herein. The controller may also store the raw fluorescence data obtained by the emission and/or reference detector(s) and other pertinent data in the memory. The controller may also store any calculated fluorescence values and/or concentration data in the memory.

Figure 9A:
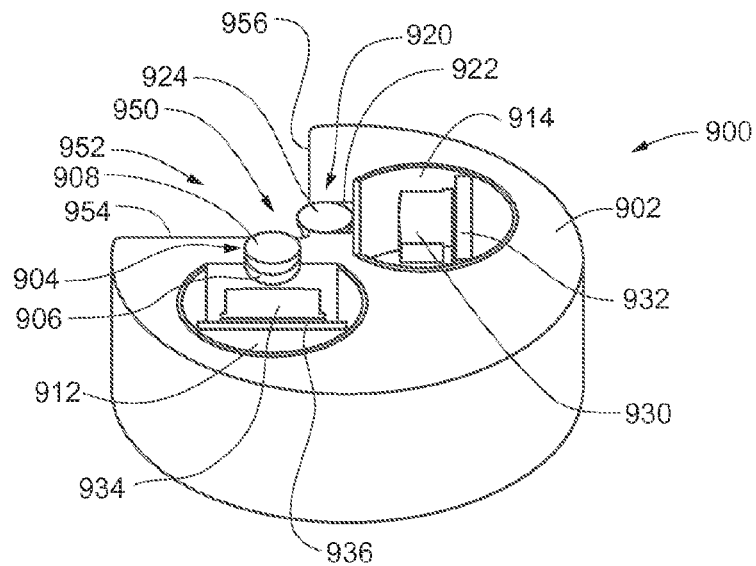
FIG. 9A is a perspective, cross-sectional view of a sensor head according to some embodiments of the invention.
Figure 9B:
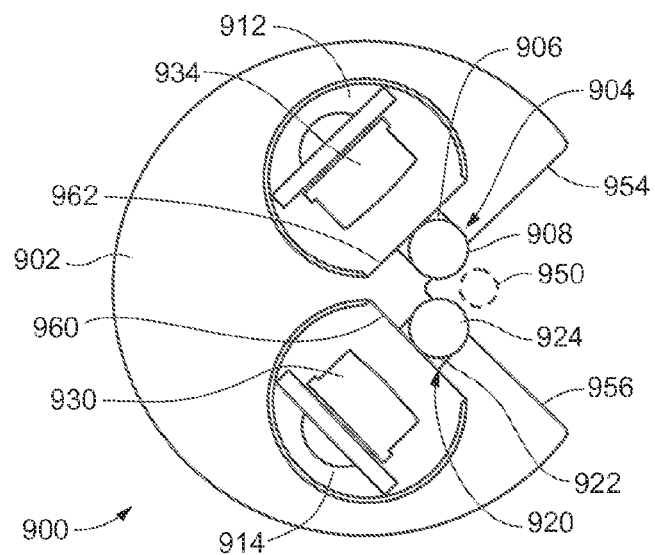
FIG. 9B is a cross-sectional view showing the sensor head of FIG. 9A.

Turning to FIGS. 9A-9B, perspective and top cross-sectional views, respectively, of an immersible sensor head 900 similar to the sensor head 700 shown in FIGS. 7A-7C are shown according to some embodiments of the invention. The sensor head 900 generally includes a housing 902, a light source chamber 912, and a detector chamber 914. The light source chamber 912 includes a light source 934 coupled to a light source board 936, similar to the light source board 500 and light source 504 shown in FIG. 5. The detector chamber 914 includes a detector 930 coupled to a detector board 392, similar to the emission detector board 600 and emission detector 604 shown in FIG. 6. The sensor head 900 also includes a light source window 904 that transmits light from the light source 934 to an analytical area 950 outside the sensor head 900 and a detector window 920 that transmits light from the analytical area 950 to the detector chamber 914 and the detector 930.

According to some embodiments, the immersible sensor head 900 is capable of measuring fluorescent emissions from a water sample within the analytical area 950 and generating a signal that corresponds to the fluorescence of the water sample. As discussed above herein, such capability can be useful for quantifying a concentration of one or more products within the water sample. In operation, for example, the light source 934 may generate UV excitation radiation that the light source window 904 transmits to the analytical area 950. In some cases an excitation filter is placed between the light source 934 and the light source window 904, similar to the embodiment shown in FIGS. 5B and 5C. In some cases the excitation radiation stimulates a fluorescent response in the water sample occupying the analytical area 950, which the detector window 920 transmits to the detector 930. In some cases one or more emission filters are placed between the detector window 920 and the detector 930, similar to the embodiment shown in FIG. 6B. The detector 930 then generates an electrical signal corresponding to the intensity of the fluorescent emissions. The detector 930 is further coupled with a controller that can then calculate the concentration of the product(s) based on the intensity of the fluorescent emissions.

In some embodiments, the sensor head 900 is provided within a handheld fluorometer such as the fluorometer 100 described above with reference to FIG. 1. As such, the detector 930 may be coupled with a controller located within a controller module portion (e.g., handle) of the fluorometer. In some embodiments, the sensor head configuration may be incorporated into a dip probe that communicates (e.g., via cable, wireless transmissions, etc.) with a base controller. For example, in some embodiments the immersible sensor head 900 may be incorporated into a fluorometer similar to those described in commonly-assigned U.S. Pat. No. 7,550,746 and/or U.S. Patent Application Publication 2009/0212236. In some cases the sensor head 900 may be coupled with a personal computer that provides the controller functionality. It should be appreciated that other arrangements are also possible and the scope of the invention is not limited to any specific controller configuration.

Returning to FIGS. 9A and 9B, in some embodiments the sensor head 900 includes a cutout 952 in a lateral surface of the housing 902. In some cases the cutout 952 generally defines a first wall 954 having a planar exterior surface and a second wall 956 having a planar exterior surface that intersects the exterior surface of the first wall 954 at a first angle (i.e., the first wall 954 and the second wall 956 form the first angle). The light source window 904 is located within the first wall 954 and provides a path for light transmission through the first wall between the analytical area 950 generally located in the cutout and the light source chamber 912 within the sensor head 900. The detector window 920 is located within the second wall 956 and provides a path for light transmission through the second wall between the analytical area 950 and the detector chamber 914 within the sensor head 900.

In some embodiments of the invention, the light source window 904 and/or the detector window 920 include a combination of a channel through the sensor head housing and a transmission element such as a window or lens that closes the channel while also transmitting light through the channel. As shown in FIGS. 9A and 9B, the light source window 904 is formed from a first channel 906 extending through the first wall 954 between the light source chamber 912 and the exterior of the sensor head 900, and a first ball lens 908 positioned in the first channel 906. In a similar manner, the detector window 920 is formed from a second channel 922 extending through the second wall 956 between the detector chamber 914 and the exterior of the sensor head 900, and a second ball lens 924 positioned in the second channel 922.

In some embodiments the sensor head 900 is preferably an immersible sensor head, meaning that it is partly or wholly immersed below the surface of the water sample during measurements. Accordingly, the light source window 904 and detector window 920 may be sealed in order to provide a substantially impermeable seal between the light source and detector chambers and the exterior of the sensor head. As previously mentioned, in some embodiments the windows may be sealed with O-rings and/or other sealing components.

The light source window 904 and the detector window 920 may also be sealed due to a pressure fit between the window channels and the ball lenses positioned within the channels, without the need for any additional sealing components such as O-rings. In some cases the first and the second walls 954, 956 of the housing may comprise a somewhat resilient or deformable material (e.g., a plastic) that allows the window channels to distend about and secure the ball lenses within the channels. For example, in some embodiments the first ball lens 908 has a radius $R_1$, while the first channel 906 has a nominal diameter less than $2R_1$. At the position of the ball lens, the channel bulges beyond its nominal diameter to accommodate the larger diameter of the ball lens. The channel thus deforms about the ball lens, securing it within the channel 906. In some cases the deformation of the first channel 906 and the corresponding pressure fit between the ball lens 908 and the channel 906 creates and/or completes a continuous impermeable seal about the first ball lens 908 between the light source chamber 912 and the analytical area exterior of the sensor head.

In some embodiments the nominal diameter of the first channel 906 is from about $1.75R_1$ to about $1.95R_1$. In some cases the radius $R_1$ of the first ball lens 908 is from about 1 mm to about 4 mm. It should be appreciated that other radii are possible for $R_1$, as are possible diameters for the first channel.

A similar seal may be created about the second ball lens 924. For example, in some embodiments the second ball lens 924 has a radius $R_2$, while the second channel 922 has a nominal diameter less than $2R_2$. At the position of the second ball lens, the channel bulges beyond its nominal diameter to accommodate the larger diameter of the second ball lens. The second channel thus deforms about the ball lens, securing it within the second channel 922. In some cases the deformation of the second channel 922 and the corresponding pressure fit between the second ball lens 924 and the second channel 922 creates and/or completes a continuous impermeable seal about second ball lens 924 between the detector chamber 914 and the analytical area exterior of the sensor head.

In some embodiments the nominal diameter of the second channel 922 is from about $1.75R_2$ to about $1.95R_2$. In some cases the radius $R_2$ of the second ball lens 924 is from about 1 mm to about 4 mm. The radius $R_2$ of the second ball lens 924 may also be the same as the radius $R_1$ of the first ball lens 908, although this is not required. It should be appreciated that other radii are possible for $R_2$, as are possible diameters for the second channel.

Embodiments of the invention provide enhanced sensitivity due in part to the immediate proximity of the water sample to the light source/emission detector windows, which dramatically decreases the travel distance between the light source/emission detector and the product within the water sample. Accordingly, the heightened sensitivity provided in embodiments of the invention is useful for measuring very low concentrations of product (e.g., parts per million, ppm) and/or for measuring concentrations of product within a water sample having high color and/or turbidity. According to some embodiments of the invention, the seal created by the pressure fit between one or more of the ball lenses and the channels allows improved positioning of the ball lenses when compared with designs incorporating a separate sealing component such as an O-ring. For example, the lack of a separate O-ring can allow one or both of the ball lenses to be positioned closer to the analytical area 950, thus decreasing transmission length and increasing operational efficiency even further, especially for measurements of water samples with high color and/or turbidity. In some embodiments the analytical distance may be from about five to about ten times shorter than in previous designs.

Referring to FIG. 9B, in some embodiments of the invention one or more of the ball lenses 908, 924 protrudes from the housing of the sensor head, thus decreasing the distance to the analytical area 950. In some cases the first ball lens 908 partially protrudes from the first channel 906 such that a plane of the exterior surface of the first wall 954 intersects the first ball lens 908. The second ball lens 924 similarly protrudes from the second channel 922 such that a plane of the exterior surface of the second wall 956 intersects the second ball lens 924. The positioning of the first and/or the second ball lenses 908, 924 within their respective channels may vary depending upon the length of the channel (e.g., the width of the first and the second walls 954, 956) and the diameter of the ball lenses. For example, in some cases the first ball lens 908 may be positioned within the first channel 906 so that one side of the ball lens protrudes past the exterior surface of the first wall 954, while a planar interior surface 962 of the first wall is tangent to or flush with the exterior surface of the opposite side of the ball lens. In some cases the second ball lens 924 is similarly positioned within the second channel 922, with a planar interior surface 960 tangent to or flush with the exterior surface of the second ball lens 924.

Figure 10A:
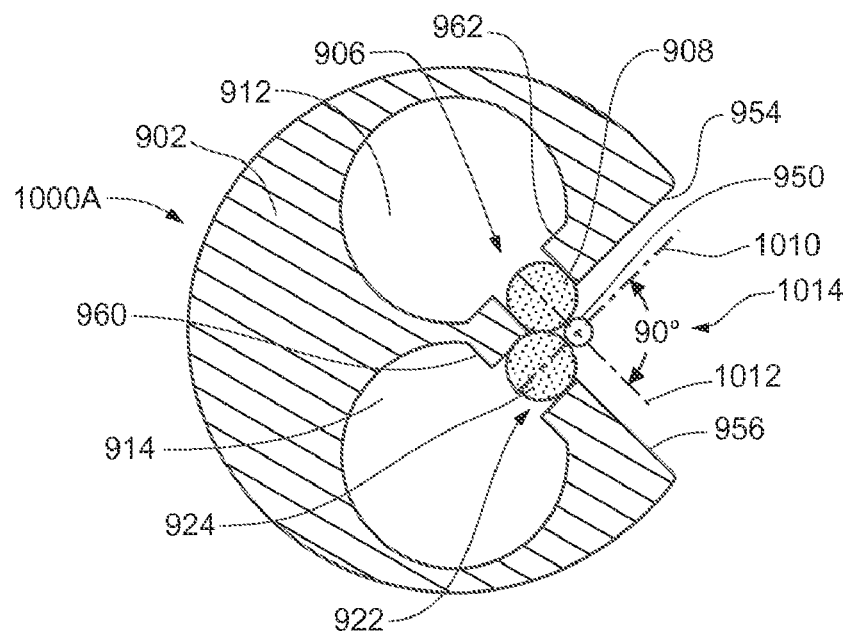
FIGS. 10A-10C are cross-sectional views of sensor heads according to some embodiments of the invention.
Figure 10B:
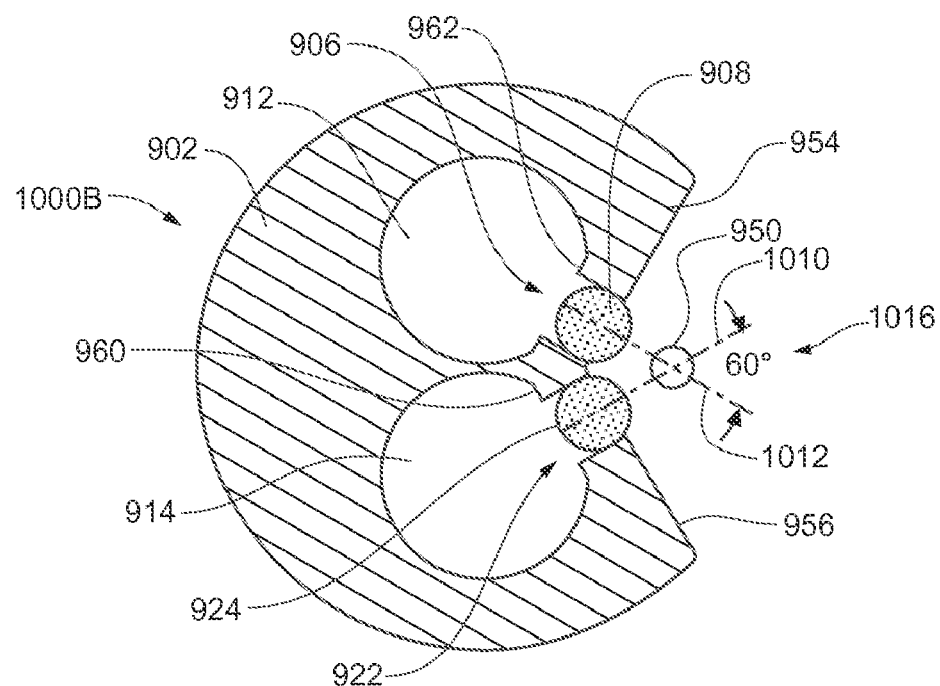
Figure 10C:
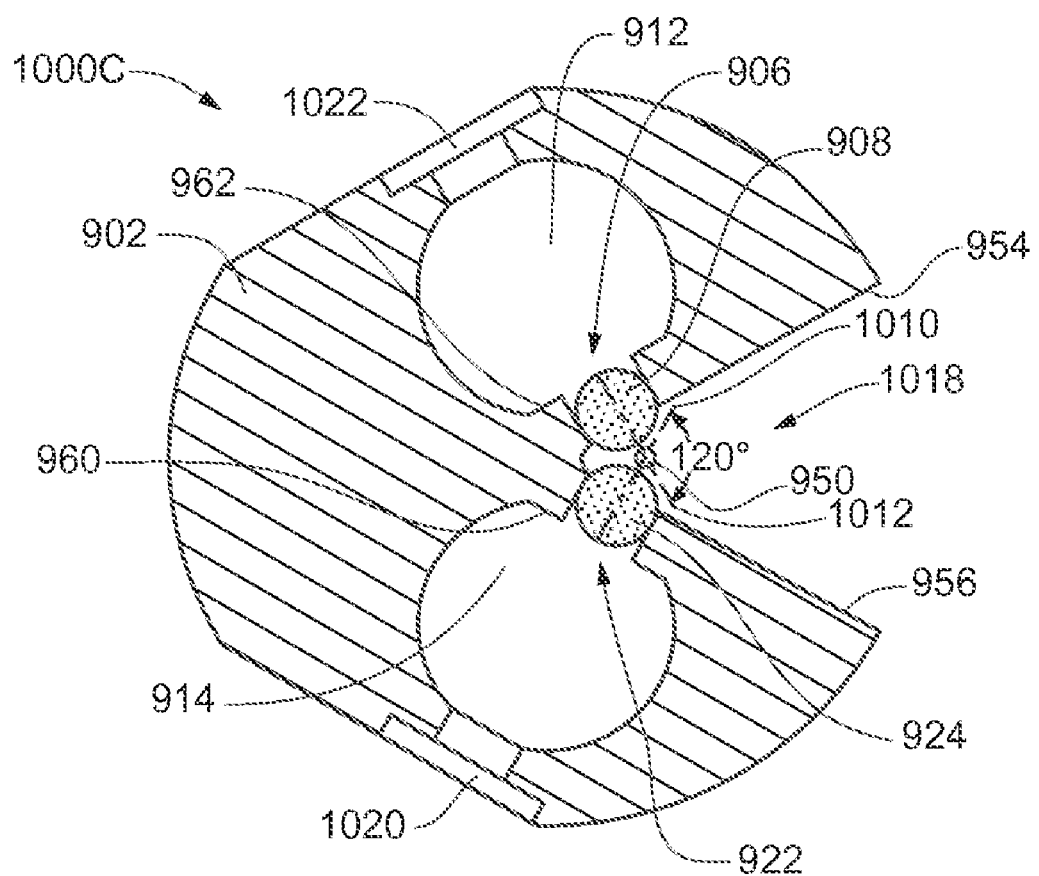

FIGS. 10A-10C are cross-sectional views of sensor heads having different angular cutouts and optics arrangements according to some embodiments of the invention. FIG. 10A illustrates a sensor head 1000A having a cutout 1014 in which the first wall 954 and the second wall 956 form an angle of approximately 90 degrees. An axis 1012 of the light source window channel crosses an axis 1010 of the detector window channel at an intersect point within the analytical area 950 exterior the sensor head. As shown in this embodiment, the first and the second channels 906, 922 are positioned within the first and the second walls 954, 956 such that the axes 1012, 1010 of the first and the second channels are orthogonal to the exterior surfaces of the first and the second walls 954, 956, though an orthogonal relationship is not required.

The angle of the cutout 1014 (i.e., between the first wall 954 and the second wall 956) and/or the angle of intersection of the first and the second channel axes 1012, 1010 can vary in different embodiments of the invention. For example, in some cases the angles between the channels and/or cutout walls may be from about 60 degrees to about 120 degrees. It should be appreciated that for orthogonal channels, the intersection angle of the channels will complement the angle of the first and the second walls (i.e., both angles add to 180 degrees in such a case).

As shown in FIG. 10A, both the angle of the cutout 1014 and the angle of intersection between the channel axes is about 90 degrees. The right angle geometry between the light source channel and the detector channel can further increase efficiency of operation by minimizing the amount of excitation light that enters the detector channel, especially when compared to a 180 degree arrangement provided in some existing optical sensors. Of course, embodiments of the invention are not limited to a particular angular orientation, and may be configured depending upon the desired parameters for a particular embodiment. FIGS. 10B and 10C illustrate two additional embodiments. In FIG. 10B, a sensor head 1000B is provided with an angular cutout 1016 forming an angle of about 120 degrees, while the axes 1012, 1010 of the first and the second channels 906, 922 form an angle of about 60 degrees. In FIG. 10C, a sensor head 1000C is provided with an angular cutout 1018 forming an angle of about 60 degrees, while the axes 1012, 1010 of the first and the second channels 906, 922 form an angle of about 120 degrees.

As mentioned above herein, some embodiments of the invention can allow one or both of the ball lenses to be positioned closer to the analytical area 950, thus decreasing transmission length through the water sample between the analytical area 950 and the ball lenses. For example, in some cases the intersect point of the channel axes is a distance of about $R_1$ to about $3R_1$ from the exterior surface of the first wall 954 and a distance of about $R_2$ to about $3R_2$ from the exterior surface of the second wall 956. In some embodiments the intersect point is a distance of about $1.2R_1$ to about $3.2R_1$ from a center of the first ball lens 908 and a distance of about $1.2R_2$ to about $3.2R_2$ from a center of the second ball lens 924. In some embodiments, both the first ball lens 908 and the second ball lens 924 are less than about 2 mm from the intersect point. As shown in FIG. 10A, in some cases the first ball lens 908 may actually contact the second ball lens 924. It should also be appreciated that while FIGS. 10A-10C show symmetrical configurations of the first ball lens, wall, and channel and the second ball lens, wall, and channel, the optical arrangement may not be symmetrical in some embodiments.

FIG. 11 is a flow diagram illustrating a method 1100 of making a sensor head according to some embodiments of the invention. The method includes initially providing (1102) a workpiece from which the sensor head will be fashioned. In some embodiments the workpiece is preferably a moldable and/or millable opaque plastic, such as Polyvinylidene Fluoride (PVDF), polyvinyl chloride (PCV), Polyoxymethylene, or Polyacetal. In some embodiments the plastic is opaque to the light wavelengths to which emission detector is sensitive and/or to light wavelengths generated by the light source within the sensor head. Of course other plastics are also possible, and in some cases any opaque plastic that is compatible with the chemical processes occurring within the sample can be used. Other materials known in the art (both polymeric and non-polymeric) are also possible. In some embodiments the sensor head is made by milling a solid workpiece, although in some embodiments, the workpiece may also be formed through molding.

The method 1100 further includes forming both a light source chamber (1104) and a detector chamber (1106) in the workpiece. For example, substantially cylindrical chambers, chambers with one or more flat interior surfaces such as those described above herein, or any other chamber(s) suitable for housing the sensor electronics may be formed. A cutout is also formed (1108) in a lateral surface of the workpiece. The cutout and the light source chamber define a first wall with an exterior planar surface and a second wall with an exterior planar surface that intersects the surface of the first wall at a first angle. The method also includes forming (1110) a light source window in the first wall and forming (1112) a detector window in the second wall. A UV light source is positioned (1114) in the light source chamber and a UV detector is positioned (1116) in the detector chamber. The UV light source emits a first UV wavelength through the light source window for excitation of a water sample within an analytical area proximate the sensor head that is detected at a second UV wavelength through the detector window from the analytical area.

According to some embodiments, forming the light source and/or detector windows includes forming (e.g., milling, etching, molding, etc.) a channel through the first and/or second wall respectively, and positioning a ball lens within each channel. In some cases the channel and/or ball lens may be similar to those described above herein.

Figure 12A:
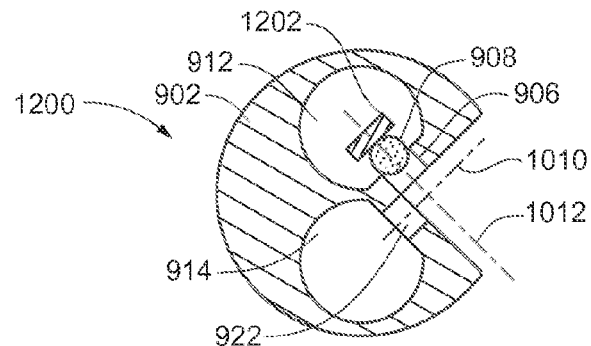
FIGS. 12A-12C are cross-sectional views of a sensor head illustrating positioning of a ball lens according to some embodiments of the invention.
Figure 12B:
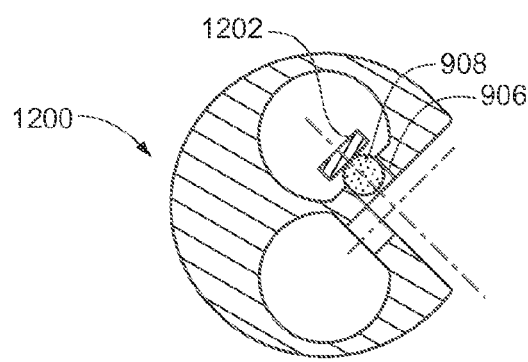
Figure 12C:
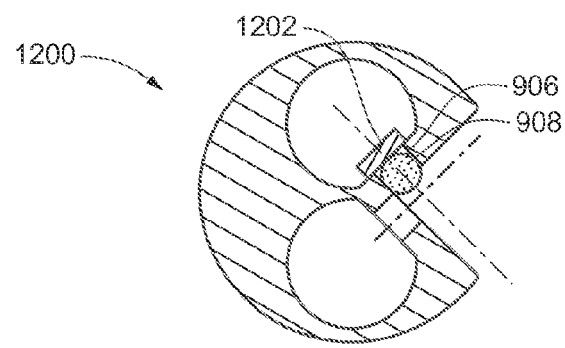

Referring to FIGS. 12A-12C, cross-sectional views of a sensor head 1200 illustrate positioning of a ball lens 908 according to some embodiments of the invention. As discussed above, in some cases the first and/or the second channel 906, 922 have a nominal diameter smaller than the diameter of the ball lens positioned within the channel. In some embodiments, a first ball lens 908 is positioned within the light source window channel 906 by inserting the ball lens into the channel 906 from inside the light source chamber 912 (FIG. 12A), and then pushing the first ball lens into the channel so that the ball lens is positioned flush with an interior surface of the chamber/wall and protruding out of the exterior surface of the wall (FIG. 12C).

As the ball lens 908 is pushed into the channel 906, the surface of the channel preferably deforms to allow passage of the ball lens. For example, pushing a glass or sapphire ball lens through a channel formed in plastic can deform the channel as the ball lens passes through the channel. In some cases the material of the channel wall also springs back to its nominal diameter as the ball lens passes through the channel. When the ball lens is in its final position, the channel remains deformed about the ball lens (e.g., on the inside and outside of the ball lens) thus securing the ball lens 908 within the channel 906 and creating a substantially continuous, impermeable seal about the ball lens between the light source chamber and the exterior of the sensor head. A similar method can be used to position a ball lens within the detector channel 922.

Referring to FIGS. 12A-12C, in some embodiments a tool 1202 may be used to push the ball lens 1102 into the channel 906. In some embodiments the tool 1202 may be inserted into the light source chamber 912 or the detector chamber 914 to push the ball lens from within the chamber. Referring to FIG. 10C, in some embodiments openings in the lateral surface of the sensor head housing provide access to the light source chamber 912 and the detector chamber 914 in order to machine window channels 906 and 922 and push the ball lenses from outside the chambers. After positioning the ball lenses, the openings can be sealed with stoppers 1020, 1022 or another equivalent means.

FIG. 13A is a cross-sectional view of one example of an insertion or positioning tool 1300 for positioning a ball lens 1306 within a window channel 1304 according to some embodiments of the invention. The positioning tool 1300 is preferably sized and shaped to fit within a sensor head chamber 1302 (e.g., the light source chamber and/or detector chamber). In some embodiments the tool 1300 includes a frame 1310 that movably supports a wedge 1312. A pushing component 1314 (e.g., a screw) can push down against the wedge, which is then directed laterally against the ball lens 1306 by an angled portion of the frame 1310. After pushing the ball lens into the channel, the tool 1300 can be removed and appropriate electronics mounted within the channel.

Figure 13B:
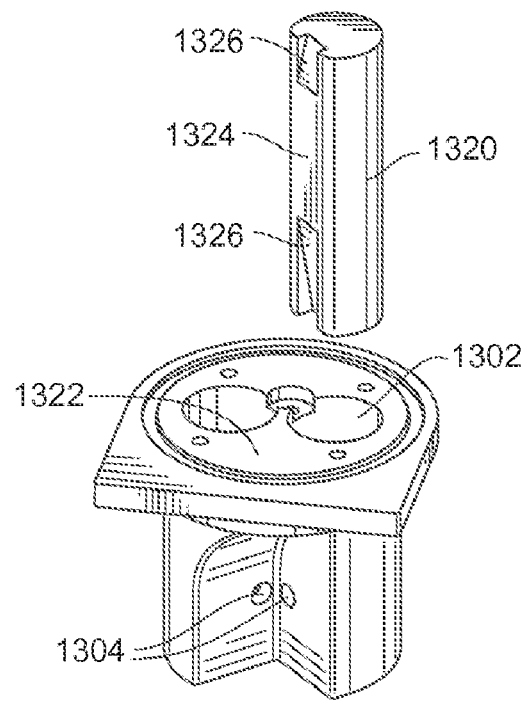
FIG. 13B is a perspective view of a sensor head and a positioning tool for positioning a ball lens according to some embodiments of the invention.
Figure 13C:
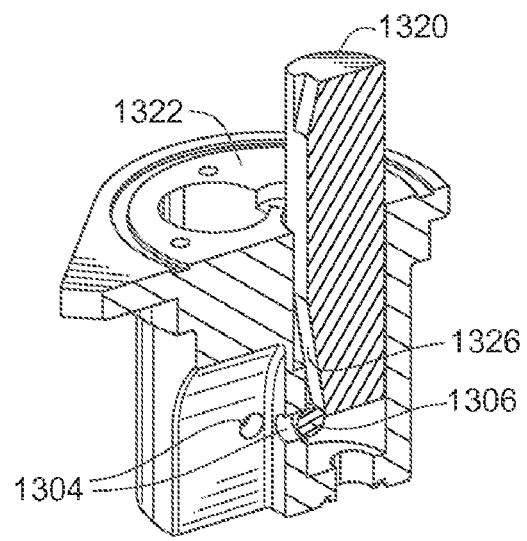
FIG. 13C is a cross-sectional view of the sensor head and positioning tool of FIG. 13B according to some embodiments of the invention.

FIGS. 13B and 13C show perspective and cross sectional views, respectively, of another example of an insertion or positioning tool 1320 for inserting a ball lens 1306 into a window channel 1304 of a sensor head 1322 according to some embodiments of the invention. The insertion tool 1320 is formed as an elongated rod or bar shaped to fit within a sensor head chamber 1302. In some cases a flat portion 1324 of the bar has a flat, tilted or angled notch 1326 near one end of the bar. When the insertion tool 1320 moves inside the sensor head chamber 1302, the flat tilted notch 1326 creates a force which pushes the ball lens 1306 into the window channel 1304. In some cases the insertion tool 1320 can have flat tilted notches 1326 of different depths and/or angles, e.g., on both ends of the bar. For example, a deeper notch can facilitate initial insertion of the ball lens into the window channel 1304 and then the insertion tool can be extracted, rotated and inserted by opposite end to use a shallower notch to ensure that the ball lens 1306 is completely inserted into the window channel 1304.

Thus, embodiments of the invention are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. A fluorometric sensor, comprising:
   an immersible sensor head, comprising:
   a housing comprising a first wall with a planar first exterior surface and a second wall with a planar second exterior surface;
   a light source chamber comprising an ultraviolet (UV) light source that emits a first UV wavelength for excitation of a water sample within an analytical area proximate the sensor head;
   a light source window positioned in the first wall that transmits the first UV wavelength from the light source chamber into the analytical area, the light source window comprising a first channel extending through the first wall and a first ball lens positioned in the first channel, the first ball lens having a radius $R_1$ and the first channel having a nominal diameter less than $2R_1$ such that the first channel is deformed about the first ball lens, securing the first ball lens within the first channel and creating a continuous impermeable seal about the first ball lens between the light source chamber and the analytical area;
   a detector chamber comprising a UV detector that detects fluorescent emissions at a second UV wavelength from the analytical area; and
   a detector window positioned in the second wall that transmits the second UV wavelength from the analytical area into the detector chamber, the detector window comprising a second channel extending through the second wall and a second ball lens positioned in the second channel, the second ball lens having a radius $R_2$ and the second channel having a nominal diameter less than $2R_2$ such that the second channel is deformed about the second ball lens, securing the second ball lens within the second channel and creating a continuous impermeable seal about the second ball lens between the detector chamber and the analytical area; and
   a controller coupled to the UV detector and adapted to calculate a concentration of a chemical in the water sample within the analytical area based on the detected fluorescent emissions.

2. The fluorometric sensor of claim 1, wherein an axis of the first channel and an axis of the second channel cross at an intersect point in the analytical area at a first angle of from about 60 degrees to about 120 degrees.

3. The fluorometric sensor of claim 2, wherein the axis of the first channel is orthogonal to the first exterior surface and the axis of the second channel is orthogonal to the second exterior surface.

4. The fluorometric sensor of claim 2, wherein the first angle is about 90 degrees.

5. The fluorometric sensor of claim 2, wherein a first distance from the intersect point to the first exterior surface is from about $R_1$ to about $3R_1$, a second distance from the intersect point to the second exterior surface is from about $R_2$ to about $3R_2$, a third distance from a center of the first ball lens to the intersect point is from about $1.2R_1$ to about $3.2R_1$, and a fourth distance from a center of the second ball lens to the intersect point is from about $1.2R_2$ to about $3.2R_2$.

6. The fluorometric sensor of claim 2, wherein each of the first ball lens and the second ball lens is less than about 2 mm from the intersect point.

7. The fluorometric sensor of claim 1, wherein $R_1$ equals $R_2$ and wherein $R_1$ and $R_2$ are from about 1 mm to about 4 mm.

8. The fluorometric sensor of claim 1, wherein the nominal diameter of the first channel is from about $1.75R_1$ to about $1.95R_1$ and the nominal diameter of the second channel is from about $1.75R_2$ to about $1.95R_2$.

9. The fluorometric sensor of claim 1, wherein the first ball lens partially protrudes from the first channel such that a plane of the first exterior surface intersects the first ball lens, and wherein the second ball lens partially protrudes from the second channel such that a plane of the second exterior surface intersects the second ball lens.

10. The fluorometric sensor of claim 9, wherein the first ball lens contacts the second ball lens.

11. The fluorometric sensor of claim 9, wherein the first wall comprises a planar first interior surface tangent to an exterior surface of the first ball lens and the second wall comprises a planar second interior surface tangent to an exterior surface of the second ball lens.

12. The fluorometric sensor of claim 1, wherein the first and the second walls comprise a resilient material and the first and the second ball lenses comprise glass or sapphire.

13. A fluorometric sensor, comprising:
an immersible sensor head, comprising:
a plastic housing comprising a cutout in a lateral surface of the housing, the cutout defining a first wall with a planar first exterior surface and a second wall with a planar second exterior surface, the first and the second exterior surfaces intersecting at a first angle;
a light source chamber comprising an ultraviolet (UV) light source that emits a first UV wavelength for excitation of a water sample within an analytical area proximate the sensor head;
a light source window positioned in the first wall that transmits the first UV wavelength from the light source chamber into the analytical area, the light source window comprising a first channel extending through the first wall orthogonal to the first exterior surface and a first ball lens positioned in the first channel, the first ball lens having a radius $R_1$ and the first channel having a nominal diameter less than $2R_1$ such that the first channel is deformed about the first ball lens, securing the first ball lens within the first channel and creating a continuous impermeable seal about the first ball lens between the light source chamber and the analytical area;
a detector chamber comprising a UV detector that detects fluorescent emissions at a second UV wavelength from the analytical area; and
a detector window positioned in the second wall that transmits the second UV wavelength from the analytical area into the detector chamber, the detector window comprising a second channel extending through the second wall orthogonal to the second exterior surface and a second ball lens positioned in the second channel, the second ball lens having a radius $R_2$ and the second channel having a nominal diameter less than $2R_2$ such that the second channel is deformed about the second ball lens, securing the second ball lens within the second channel and creating a continuous impermeable seal about the second ball lens between the detector chamber and the analytical area; and a controller coupled to the UV detector and adapted to calculate a concentration of a chemical in the water sample within the analytical area based on the detected fluorescent emissions; wherein
the first angle is from about 60 degrees to about 120 degrees,
an axis of the first channel and an axis of the second channel cross at an intersect point in the analytical area,
a first distance from the intersect point to the first exterior surface is from about $R_1$ to about $3R_1$,
a second distance from the intersect point to the second exterior surface is from about $R_2$ to about $3R_2$,
a third distance from a center of the first ball lens to the intersect point is from about $1.2R_1$ to about $3.2R_1$, and
a fourth distance from a center of the second ball lens to the intersect point is from about $1.2R_2$ to about $3.2R_2$.

14. The fluorometric sensor of claim 13, wherein the first angle is about 90 degrees.

15. The fluorometric sensor of claim 13, wherein each of the first ball lens and the second ball lens is less than about 2 mm from the intersect point.

16. The fluorometric sensor of claim 13, wherein $R_1$ equals $R_2$ and wherein $R_1$ and $R_2$ are from about 1 mm to about 4 mm.

17. The fluorometric sensor of claim 13, wherein the nominal diameter of the first channel is from about $1.75R_1$ to about $1.95R_1$ and the nominal diameter of the second channel is from about $1.75R_2$ to about $1.95R_2$.

18. The fluorometric sensor of claim 13, wherein the first ball lens partially protrudes from the first channel such that a plane of the first exterior surface intersects the first ball lens, and wherein the second ball lens partially protrudes from the second channel such that a plane of the second exterior surface intersects the second ball lens.

19. The fluorometric sensor of claim 18, wherein the first ball lens contacts the second ball lens.

20. The fluorometric sensor of claim 18, wherein the first wall comprises a planar first interior surface tangent to an exterior surface of the first ball lens and the second wall comprises a planar second interior surface tangent to an exterior surface of the second ball lens.

21. The fluorometric sensor of claim 13, wherein the first and the second walls comprise a resilient plastic and the first and the second ball lenses comprise glass or sapphire.

22. A method for making an immersible fluorometric sensor head, comprising:
providing a plastic workpiece;
forming a light source chamber in the workpiece;
forming a detector chamber in the workpiece;
forming a cutout in a lateral surface of the workpiece, the cutout and the light source chamber defining a first wall with a first exterior planar surface, the cutout and the detector chamber defining a second wall with a second exterior planar surface, the first and the second exterior planar surfaces intersecting at a first angle;
forming a light source window in the first wall, comprising forming a first channel extending through the first wall and positioning a first ball lens in the first channel, the first ball lens having a radius $R_1$ and the first channel having a nominal diameter less than $2R_1$, the positioning comprising pushing the first ball lens into the first channel from the light source chamber and deforming the first channel about the first ball lens to secure the first ball lens and create a continuous impermeable seal about the first ball lens between the light source chamber and an exterior of the sensor head;

forming a detector window in the second wall, comprising forming a second channel extending through the second wall and positioning a second ball lens in the second channel, the second ball lens having a radius $R_2$ and the second channel having a nominal diameter less than $2R_2$, the positioning comprising pushing the second ball lens into the second channel from the detector chamber and deforming the second channel about the second ball lens to secure the second ball lens and create a continuous impermeable seal about the second ball lens between the detector chamber and the exterior of the sensor head;

positioning an ultraviolet (UV) light source in the light source chamber that emits a first UV wavelength through the light source window for excitation of a water sample within an analytical area proximate the sensor head; and positioning a UV detector in the detector chamber that detects fluorescent emissions at a second UV wavelength through the detector window from the analytical area.

23. The method of claim 22, further comprising pushing the first ball lens into the first channel so that the first ball lens partially protrudes from the first channel such that a plane of the first exterior surface intersects the first ball lens, and further comprising pushing the second ball lens into the second channel so that the second ball lens partially protrudes from the second channel such that a plane of the second exterior surface intersects the second ball lens.

24. The method of claim 22, further comprising pushing the first ball lens into the first channel so that a planar first interior surface of the first wall is tangent to an exterior surface of the first ball lens, and further comprising pushing the second ball lens into the second channel so that a planar second interior surface of the second wall is tangent to an exterior surface of the second ball lens.

25. The method of claim 22, wherein the first angle is from about 60 degrees to about 120 degrees.

26. The method of claim 22, wherein an axis of the first channel is orthogonal to the first exterior surface and an axis of the second channel is orthogonal to the second exterior surface.

27. The method of claim 22, wherein $R_1$ equals $R_2$ and wherein $R_1$ and $R_2$ are from about 1 mm to about 4 mm.

28. The method of claim 22, wherein the diameter of the first channel is from about $1.75R_1$ to about $1.95R_1$ and the diameter of the second channel is between from about $1.75R_2$ to about $1.95R_2$.

29. The method of claim 22, wherein the first ball lens contacts the second ball lens.

30. The method of claim 22, wherein the first and the second walls comprise a resilient material and the first and the second ball lenses comprise glass or sapphire.

31. The fluorometric sensor of claim 1, wherein the light source chamber contains a reference detector to monitor intensity of the UV light source.

32. The fluorometric sensor of claim 31, wherein the UV light source and the reference detector are placed inside an optical cavity such that the reference detector measures UV light that is reflected and scattered inside the optical cavity.

33. The fluorometric sensor of claim 32, wherein the optical cavity is formed by a filter holder, and an excitation filter is secured inside the optical cavity opposite from the UV light source and the reference detector.

34. The fluorometric sensor of claim 32, wherein the optical cavity is formed by a cover for the UV light source and the reference detector, and an excitation filter is secured inside the optical cavity on the UV light source.

* * * * *